(12) United States Patent
Yoon et al.

(10) Patent No.: US 9,441,018 B2
(45) Date of Patent: Sep. 13, 2016

(54) GENE FROM TIDAL FLAT METAGENOME AND A NOVEL PROTEIN DISPLAYING BOTH PHOSPHOLIPASE AND LIPASE ACTIVITIES

(71) Applicant: KOREA RESEARCH INSTITUTE OF BIOSCIENCE AND BIOTECHNOLOGY, Daejeon (KR)

(72) Inventors: Jung-Hoon Yoon, Daejeon (KR); Mi Hwa Lee, Daejeon (KR); Chul Hyung Kang, Daejeon (KR); Ki Hoon Oh, Daejeon (KR); Tae Kwang Oh, Daejeon (KR)

(73) Assignee: Korea Research Institute of Bioscience and Biotechnology, Daejeon (KR)

( * ) Notice: Subject to any disclaimer, the term of this patent is extended or adjusted under 35 U.S.C. 154(b) by 0 days.

(21) Appl. No.: 14/280,062

(22) Filed: May 16, 2014

(65) Prior Publication Data
US 2015/0329840 A1 Nov. 19, 2015

Related U.S. Application Data

(63) Continuation of application No. PCT/KR2012/005705, filed on Jul. 17, 2012.

(30) Foreign Application Priority Data

Nov. 18, 2011 (KR) .................. 10-2011-0120844
Jul. 17, 2012 (KR) .................. 10-2012-0077632

(51) Int. Cl.
*D06M 16/00* (2006.01)
*C07K 14/195* (2006.01)
*C11D 3/386* (2006.01)
*C12N 9/20* (2006.01)

(52) U.S. Cl.
CPC ......... *C07K 14/195* (2013.01); *C11D 3/38627* (2013.01); *C12N 9/20* (2013.01);
(Continued)

(58) Field of Classification Search
None
See application file for complete search history.

(56) References Cited

U.S. PATENT DOCUMENTS

2008/0271207 A1  10/2008  Eastmond
2009/0203564 A1*  8/2009  Wittorff ............. C11D 3/38609
                                                                510/109

FOREIGN PATENT DOCUMENTS

EP      2302042       3/2011
WO      95/22615      8/1995

OTHER PUBLICATIONS

Lee et al., GenBank database accession No. ABY56067.1, "phospholipase A1 [uncultured bacterium pFosPlaG]" (2008).*
(Continued)

*Primary Examiner* — Erin M Bowers
(74) *Attorney, Agent, or Firm* — Lathrop & Gage LLP

(57) ABSTRACT

The present invention relates to a novel gene derived from a tidal flat metagenome, and a novel protein obtained therefrom showing the coactivity of phospholipase and lipase. Specifically, the novel gene isolated from the metagenome library of tidal flat sediments and the protein having phospholipase and lipase activities encoded from the novel gene: are expressed in a water-soluble form to be mass-producible; enable ultra high-purity protein to be obtained through single step purification using an Ni-NTA column; show good activity in the pH range of 5~10; maintain good low temperature activity and stability up to a temperature of 3° C. to 40° C.; and have high resistance against various organic solvents. Therefore, the novel gene and the protein can be usefully used for various industrial fields such as the purification and conversion of oil and fat, bio-medicine, and fine chemistry.

5 Claims, 14 Drawing Sheets

(52) U.S. Cl.
CPC ...... *C07K 2319/21* (2013.01); *C07K 2319/23* (2013.01); *C07K 2319/41* (2013.01); *C07K 2319/43* (2013.01); *C07K 2319/50* (2013.01); *C12Y 301/01003* (2013.01); *C12Y 301/01032* (2013.01)

(56) References Cited

OTHER PUBLICATIONS

Lee et al. (2008) GenBank Database Accession No. ABY56067.1, "phospholipase A1 [uncultured bacterium pFosPlaG]," 1 page.

Lee et al. (2006) "Isolation and Characterization of a Novel Lipase from a Metagenomic Library of Tidal Flat Sediments: Evidence for a New Family of Bacterial Lipases," Applied and Environmental Microbiology 72(11):7406-7409.

Lee et al. (2012) "Novel Metagenome-Derived, Cold-Adapted Alkaline Phospholipase with Superior Lipase Activity as an Intermediate Between Phospholipase and Lipase," Applied and Environmental Microbiology 78(14):4959-4966 (English Abstract only).

PCT International Search Report (2012) issued for PCT/KR2012/005705.

\* cited by examiner

Activity of the solid medium supplemented with 1% tricaplyrin

Activity of the solid medium Supplemented with 1% phosphatidylcholine the substrate specificity against various phospholipids
  PC, phosphatydilcholine;
  PE, phosphatidylethanolamine;
  PS, phosphatidylserine;
  PI, phosphatidylinositol;
  PG, phosphatidylglycerol;
  PA, phosphatidic acid

GENE FROM TIDAL FLAT METAGENOME AND A NOVEL PROTEIN DISPLAYING BOTH PHOSPHOLIPASE AND LIPASE ACTIVITIES

BACKGROUND OF THE INVENTION

1. Field of the Invention

The present invention relates to a novel protein showing both phospholipase and lipase activities, more precisely a gene isolated from the microbial metagenome of tidal flat sediment and displaying both phospholipase and lipase activities and a protein encoded therefrom showing the coactivity of calcium-dependent phospholipase and lipase.

2. Description of the Related Art

Lipase (glycerol ester hydrolase, EC 3.1.1.3) is a carboxy ester hydrolase belonging to α/β hydrolases that are able to decompose or synthesize long-chain acylglycerol. Up to date, a variety of animals, plants, and microorganisms have been confirmed to synthesize lipase. Accordingly, studies on the biochemical characteristics of lipase and on lipase genes have been actively undergoing. The endogenous lipase is not only involved in fat metabolism but also comparatively stable in organic solvents. This endogenous lipase does not need coenzymes, has wide substrate specificity and comparatively high optical specificity, making it an excellent biocatalyst for bioconversion, in the field of detergent industry, food additive production, pitch elimination in paper industry, and others. Studies have been under-going to mass-produce such industrially useable and valuable lipase with high efficiency. In particular, studies have been focused mainly on microorganisms producing lipase. Hosts capable of producing lipase are exemplified by *Candida* sp., *Bacillus* sp., *Penicilium* sp., *Mucor* sp., *Rhizopus* sp., *Pseudomonas* sp., and *Streptomyces* sp.

Lysophospholipid is generated from hydrolysis of phospholipid by phospholipase, which not only acts like a functional group in the course of platelet aggregation but also mediates various physiological activities including signal transduction or plays a role in preventing over-ripen of fruits and plants as a plant hormone. In particular, lysophospholipid has a high water-solubility and can form a stable emulsion even at different hydrogen ion concentrations and temperatures. lysophospholipid is also stable in the presence of magnesium and calcium ions, so that it has been used in the fields of medicine, cosmetics, and food industry.

The said lysophospholipid can be generated from phospholipid mediated by phospholipase in a certain biochemical pathway and at this time phospholipase A hydrolyzes 1-acyl group or 2-acyl group of phospholipid to produce lysophospholipid and fatty acid. This phospholipase A is an essential enzyme in the synthesis of phospholipid containing useful fatty acid such as polyunsaturated fatty acid (PUFA) exemplified by DHA or EPA, etc. This phospholipase A is isolated from various mammals, snake or bee venom, and microorganisms such as *Serratia* sp., *Aspergillus* sp., *Streptomyces* sp., and *Fusarium* sp. and can be applied to food industry. In order for this enzyme to be used in more industrial fields, substrate specificity or enzyme stability of this enzyme has to be improved (De Maria et al., Appl. Microbiol. Biotechnol. 74:290-300, 2007).

Both lipase and phospholipase display similar mechanism to each other. However, lipase obtained from *Staphylococcus hyicus* is the only enzyme displaying coactivity to lipid and phospholipid (van Oort et al., Biochemistry, 28:9278-9285, 1989). The enzyme originated from *S. hyicus* is hard to be produced in a large scale and has comparatively low stability, which makes it less usable in industry.

In the field of fine chemistry producing high value-added lead compounds including medicinal products, when ester compounds are synthesized by the conventional chemical method, the synthesis is achieved at high temperature under high pressure with requiring high consumption of energy, which causes many side reactions that might have a bad effect on the quality of the product. In addition, the conventional method has disadvantages of low conversion rate and low purify in some optical isomers, because of which the production of high purity fine chemical product has been troubled. To overcome the above problem, recent studies have been focused on taking advantage of such reaction that uses the enzyme displaying site specificity and optical specificity as a biocatalyst. However, this attempt has been limited in its application because of the problem of losing the enzyme activity at low temperature.

Lipase hydrolyzes lipid dirt into water-soluble fatty acid or glycerol, suggesting that it makes the function of a surfactant easy. So, lipase has been a target as a detergent or a bleach additive, which was not practical so far, though. This is because lipase loses its enzyme activity at a low washing temperature, meaning oil and fat components are not eliminated completely.

The microorganisms suitable for culture were the major targets of the attempt to find out an enzyme having excellent activity and stability. Various enzymes identified from some of those microorganisms have been used industrially. However, recent molecular-microbial ecology studies proved that at least 99% microorganisms in the natural world are not separated or identified either by the conventional culture method performed in a lab (Amann et al., Microbiol. Rev. 59: 143-169, 1995; Hugenholtz and Pace, Trends Biotechnol. 14: 190-197, 1996; Ward et al., Nature 345: 63-65, 1990). Therefore, a new attempt has been made to search novel genes that could not been identified because of the difficulty in culture from the library constructed by using metagenome, the genome of the microorganisms extracted directly from the natural world without the process of culture and further to develop useful materials therefrom.

Metagenome is the definition indicating the genome of all microorganisms existing in the natural world. In general, the metagenome study is composed of the following steps; isolating metagenome from microorganisms in the natural world without culture; constructing library thereof; and introducing the library into *E. coli* suitable for culture. This method is to obtain useful materials from those microorganisms which could not be cultured. Even though it is very hard to obtain information about such microorganism, the origin of a target gene, this method has the advantage of obtaining the useful product and gene of the microorganism at the same time.

A research team at University of Wisconsin, USA, was the first study group who succeeded in isolation of massive metagenome and thereafter constructed metagenome library by cloning the metagenome into bacterial artificial chromosome (BAC) vector. They also succeeded in isolation of broad spectrum antibiotics and the genes involved therein (Gillespie et al., Appl. Environ. Microbiol. 68: 4301-4306, 2002; Rondon et al., Appl. Environ. Microbiol. 66: 2541-2547, 2000). A TIGR (The Institute for Genomic Research) team also constructed the general marine microorganism metagenome library in BAC vector to screen genetic resources of those marine microorganisms that could not be cultured so far.

The present inventors isolated a novel gene from the microbial metagenome library obtained from the tidal flat sediment where have a unique microbial diversity including the various unculturable microorganisms, constructed a vector containing the said gene, transfected E. coli with the vector, and accordingly confirmed that the protein produced from the transformant constructed above displayed excellent phospholipase and lipase activities together and had excellent activity and stability as well even at a low temperature and in alkali condition, leading to the completion of the present invention.

SUMMARY OF THE INVENTION

It is an object of the present invention to provide a novel gene isolated from the metagenome of tidal flat sediment microorganisms, a recombinant vector containing the gene, a transformant transfected with the said vector, and a polypeptide encoded from the said gene having both phospholipase and lipase activities.

It is another object of the present invention to provide a detergent additive containing the polypeptide of the invention having both phospholipase and lipase activities as an active ingredient.

It is also an object of the present invention to provide a washing method including the step of treating the surface of a material with the polypeptide of the invention having both phospholipase and lipase activities.

It is further an object of the present invention to provide a use of the polypeptide of the invention having both phospholipase and lipase activities for the preparation of a detergent.

To achieve the above objects, the present invention provides a polypeptide composed of the amino acid sequence represented by SEQ. ID. NO: 5 and having both phospholipase and lipase activities.

The present invention also provides a polynucleotide encoding the polypeptide of the present invention.

The present invention further provides a recombinant expression vector containing the polynucleotide of the present invention.

The present invention also provides a transformant prepared by transfecting a host cell with the recombinant expression vector of the present invention.

The present invention also provides a preparation method of a recombinant protein having both phospholipase and lipase activities which comprises the following steps:

1) constructing a recombinant expression vector containing the polynucleotide of the present invention;

2) preparing a transformant by introducing the recombinant expression vector above into a host cell; and, 3) culturing the transformant and inducing the expression of the recombinant protein therein, followed by obtaining the expressed recombinant protein.

The present invention also provides a detergent additive containing the polypeptide of the invention having both phospholipase and lipase activities as an active ingredient.

The present invention also provides a washing method including the step of treating the surface of a material with the polypeptide of the invention having both phospholipase and lipase activities.

In addition, the present invention provides a use of the polypeptide of the invention having both phospholipase and lipase activities for the preparation of a detergent.

Advantageous Effect

As explained hereinbefore, the novel gene isolated from the metagenome library of tidal flat sediment microorganisms and the protein having phospholipase and lipase activities encoded from the novel gene: are expressed in a water-soluble form to be mass-producible; enable ultra high-purity protein to be obtained through single step purification using an Ni-NTA column; show good activity in the pH range of 5~10; maintain good low temperature activity and stability up to a temperature of 3° C. to 40° C.; and have high resistance against various organic solvents. Therefore, the novel gene and the protein can be usefully used for various industrial fields such as the purification and conversion of oil and fat, bio-medicine, and fine chemistry.

BRIEF DESCRIPTION OF THE DRAWINGS

The application of the preferred embodiments of the present invention is best understood with reference to the accompanying drawings, wherein.

ZP_02001945: *Beggiatoa* sp. PS derived secreted protein;

EBL22535: marine metagenome derived hypothetical protein;

AAD10476: *Serratia* sp. MK1 derived phospholipase A1;

AAM13978: *Serratia marcescens* derived phospholipase;

YP_001005338: *Yersinia enterocolitica* 8081 derived phospholipase A; and

YP_001479905: *Serratia proteamaculans* 568 derived phospholipase A1;

The amino acids marked by * indicate well-preserved lipase specific catalytic triad and the underlined part indicates common amino acid sequences in around Ser of phospholipase A1.

Figure 2:
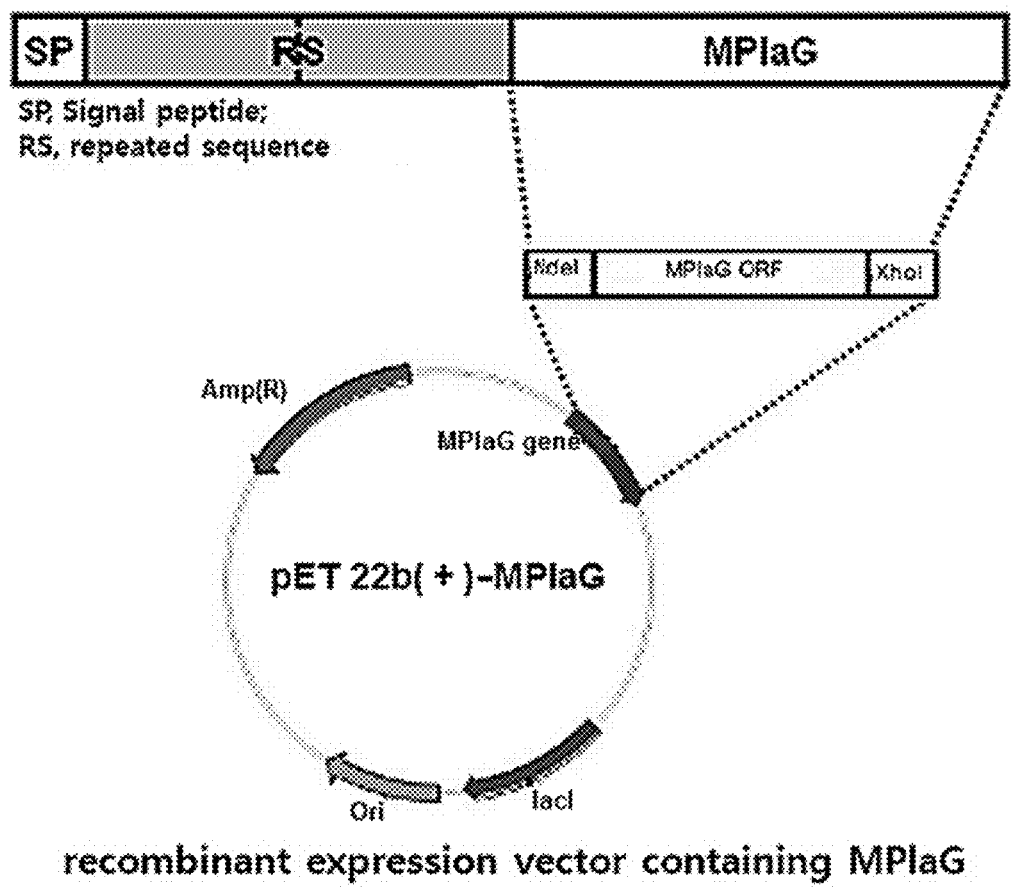

FIG. 2 is a schematic diagram illustrating the recombinant vector pET22b(+)-MPIaG containing the catalytic domain MPIaG of the novel PlaG gene originated from the metagenome library of tidal flat sediment microorganisms.

Figure 3:
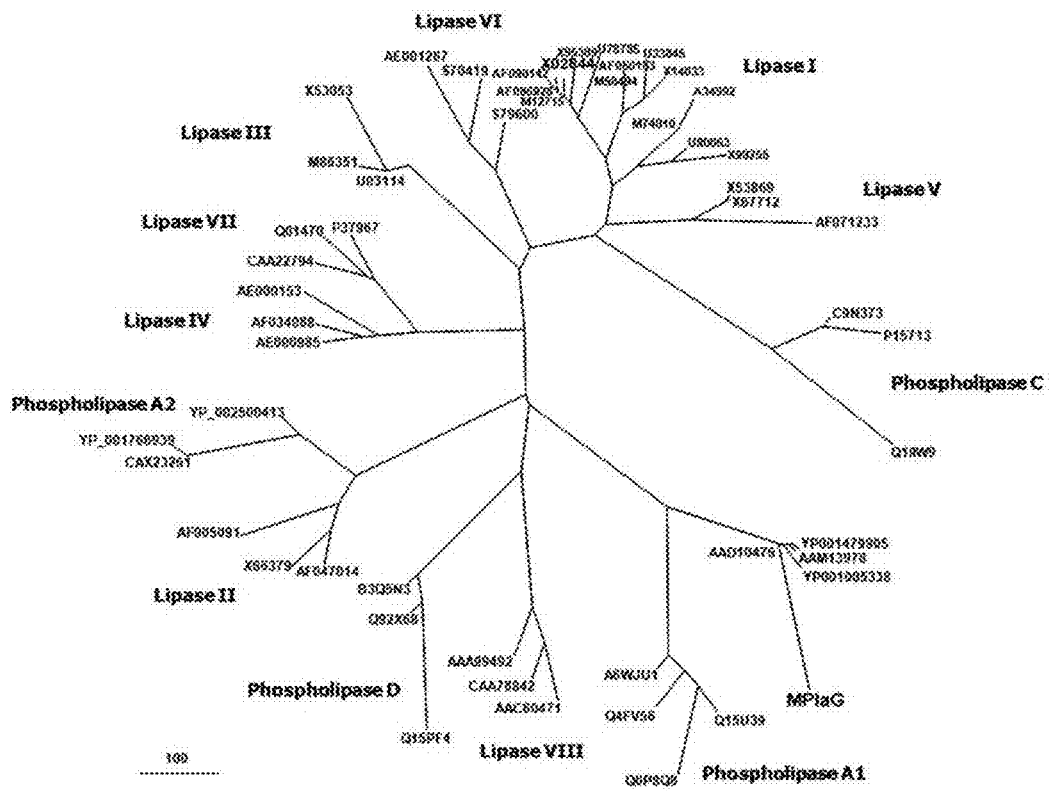

FIG. 3 is a diagram illustrating the phylogenetic tree of the phospholipase/lipase MPIaG (the protein PlaG having both phospholipase and lipase activities) derived from tidal flat metagenome, various lipases selected from the conventional lipase family, homologous phospholipases with phospholipase/lipase MPIaG, and other known phospholipases; The phylogenetic tree was constructed by using the program MEGALIGN and the bar indicates amino acid substitution.

Figure 4:
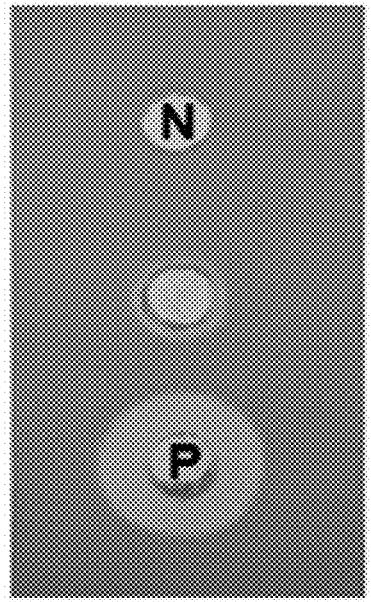
Figure 4:
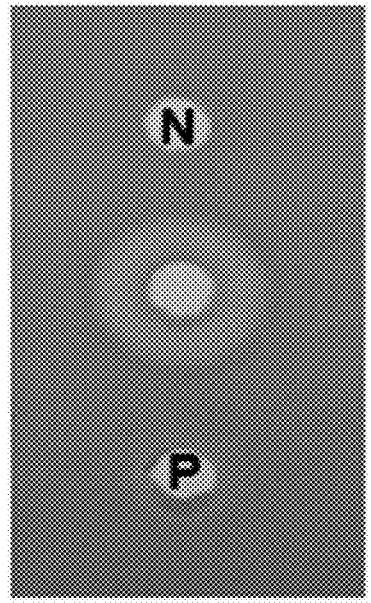

FIG. 4 is a set of photographs illustrating the activity of the phospholipase/lipase MPIaG of the present invention on the solid medium supplemented with tricaprylin or phosphatidylcholine emulsion. Cell lysate of *E. coli* BL21(DE3), the host cell used for transformation, was used as the negative control, while *Candida antarctica* lipase B (CALB) was used as the lipase-positive control.

Figure 5:
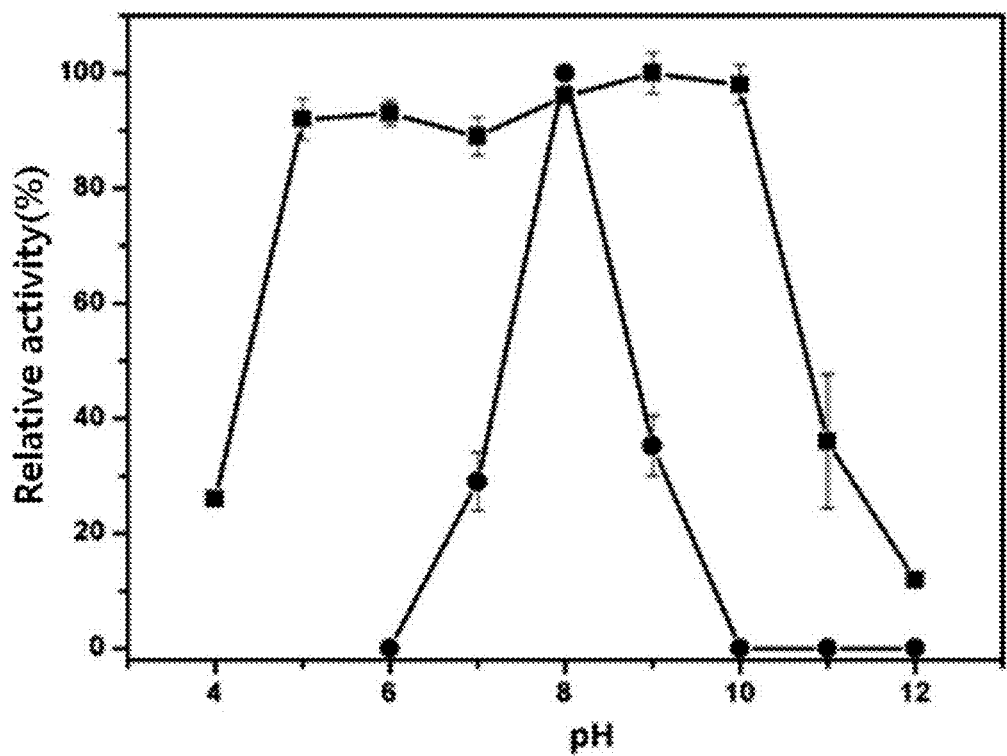

FIG. 5 is a graph illustrating the pH dependent activity (●) and stability (■) of the phospholipase/lipase MPIaG of the present invention.

Figure 6:
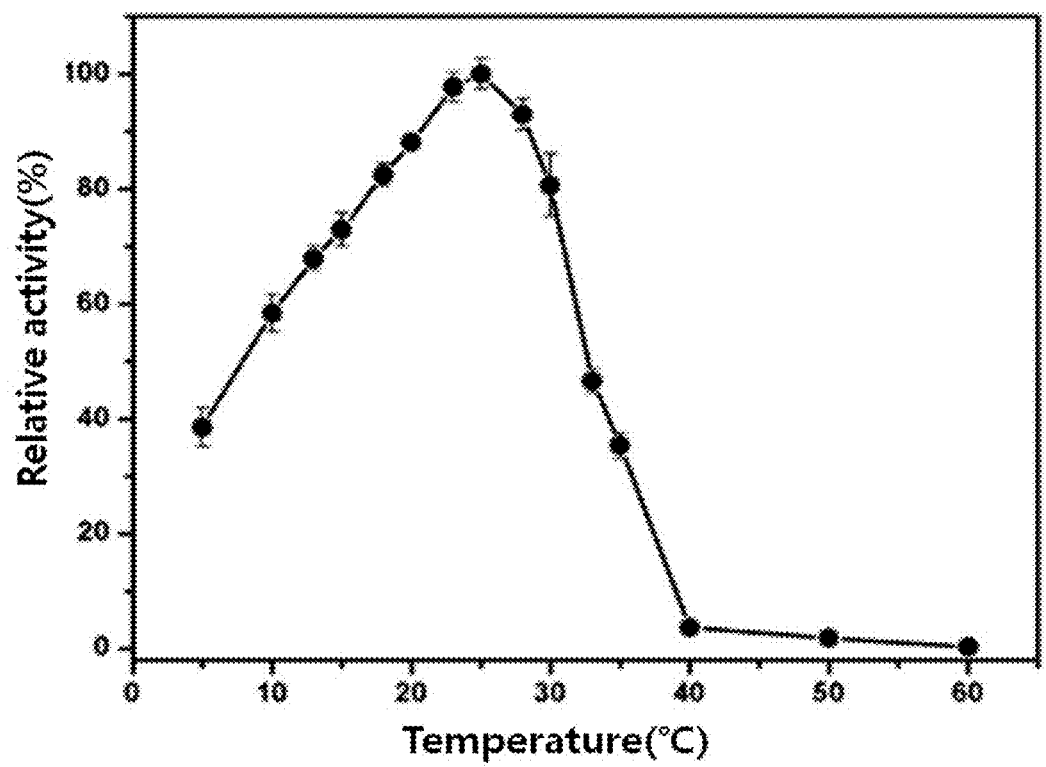

FIG. 6 is a graph illustrating the temperature dependent activity of the phospholipase/lipase MPIaG of the present invention.

Figure 7:
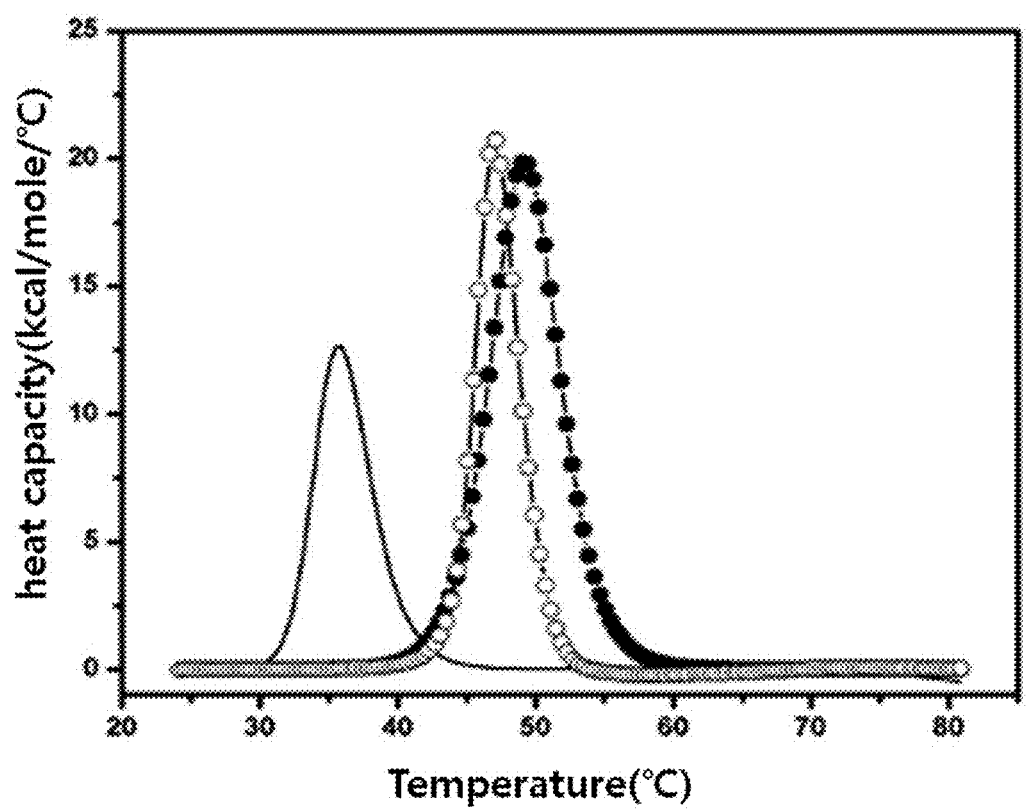

FIG. 7 is a graph illustrating the changes of melting temperature of the phospholipase/lipase MPIaG of the present invention according to 0 mM (-), 2 mM (○), and 5 mM (●) of calcium.

Figure 8:
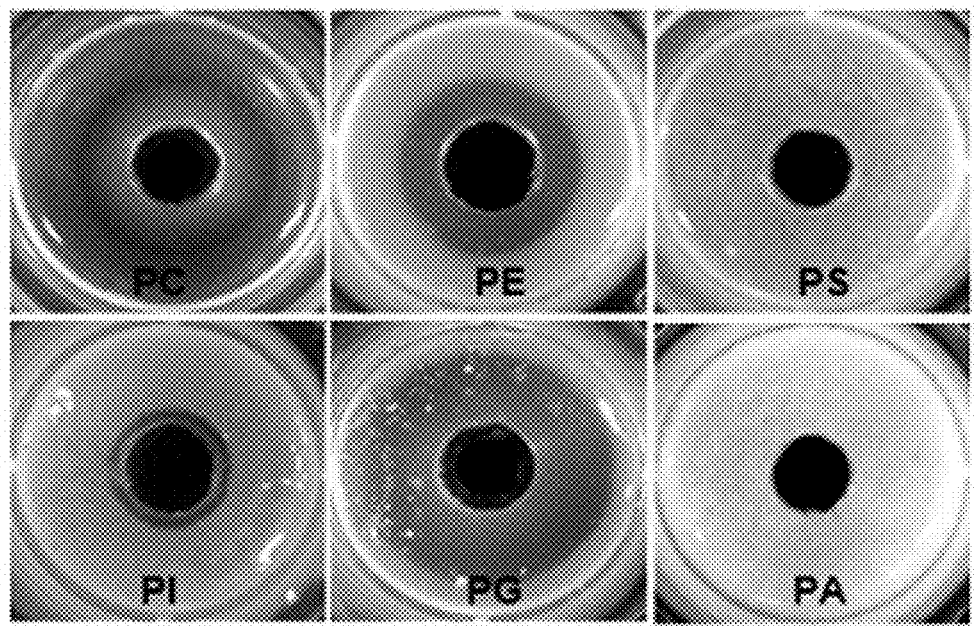

FIG. 8 is a set of photographs illustrating the substrate specificity of the phospholipase/lipase MPIaG of the present invention against various phospholipids.

Figure 9A:
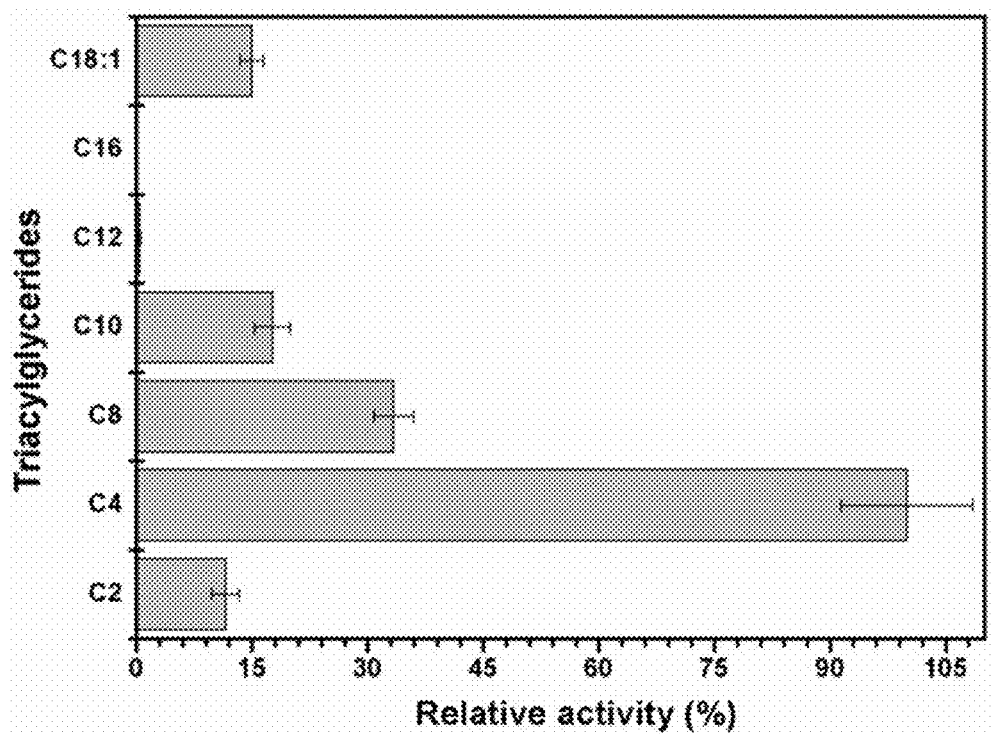
Figure 9B:
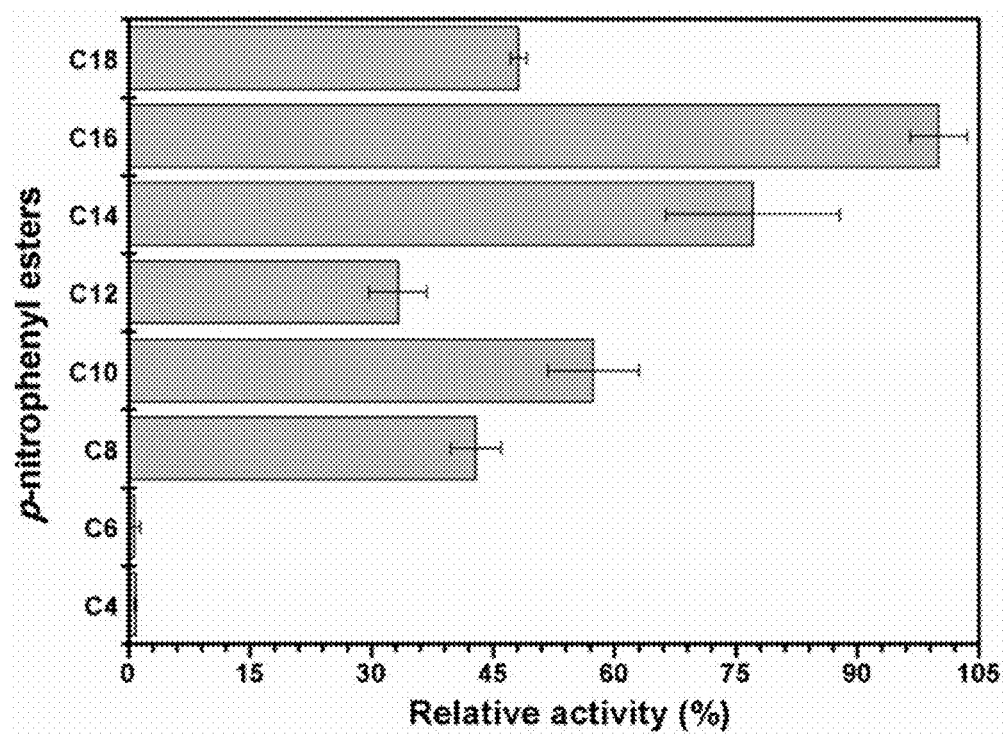
Figure 9C:
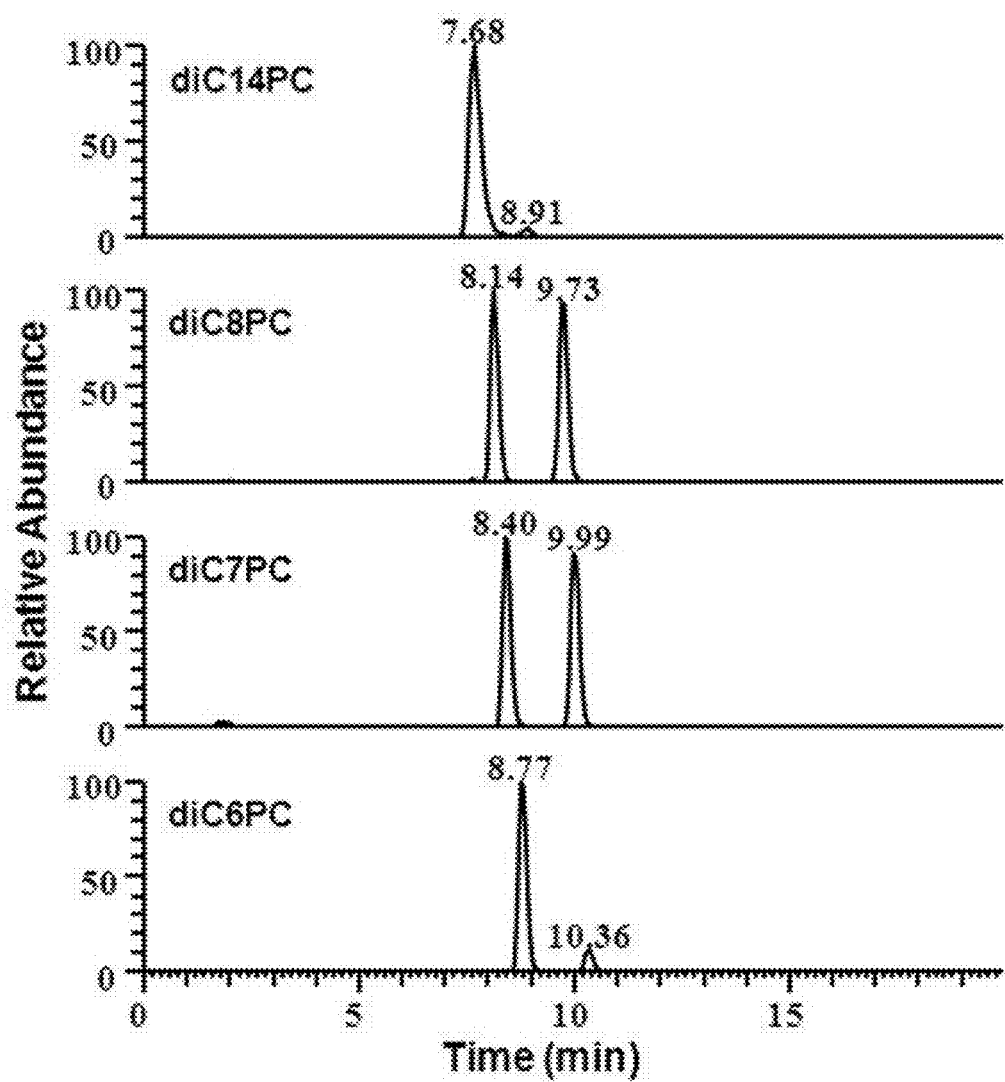

FIG. 9A, FIG. 9B and FIG. 9C are a set of graphs illustrating the chain-length specificity of MPIaG to triglyceride (a), para-nitrophenyl ester (b) and phosphatidylcholine (c), measured by pH-titration, spectrometry, and LC-MS; The vertical and horizontal lines in (a) and (b) indicate the substrate carbon chain length and the relative activity to the maximum activity (100%), respectively; In LC-MS, respectively, the reaction products of MPIaG to phosphatydilcholine were isolated by HPLC as follows:

diC6PC, 8.77 min (1,2-dihexanoyl-phosphatidylcholine, m/z 498, 89.6%) and 10.36 min (2-hexanoyl-lysophosphatidylcholine, m/z 400, 10.4%); diC7PC, 8.40 min (1,2-diheptanoyl-phosphatidylcholine, m/z 526, 50.5%) and 9.99 min (2-heptanoyl-lysophosphatidylcholine, m/z 414, 49.5%); diC8PC, 8.14 min (1,2-dioctanoyl-phosphatidylcholine, m/z 554, 49.6%) and 9.73 min (2-octanoyl-lysophosphatidylcholine, m/z 428, 50.4%); diC14PC, 7.68 min (1,2-dimyristoyl phosphatidylcholine, m/z 722, 96.5%) and 8.91 min (2-myristoyl-lysophosphatidylcholine, m/z 512, 3.5%).

Figure 10:
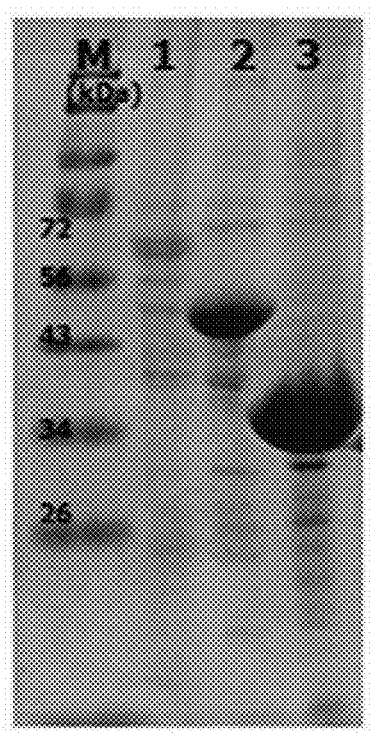

FIG. 10 is a photograph illustrating the result of SDS-PAGE (sodium dodecylsulfate-polyacrylamide gel electrophoresis) performed to confirm the purified phospholipase/lipase MPIaG of the present invention:

M: size marker;
Lane 1: full-length phospholipase/lipase PlaG;
Lane 2: truncated protein 1; and
Lane 3: truncated protein 2 (phospholipase/lipase MPIaG).

Figure 11A:
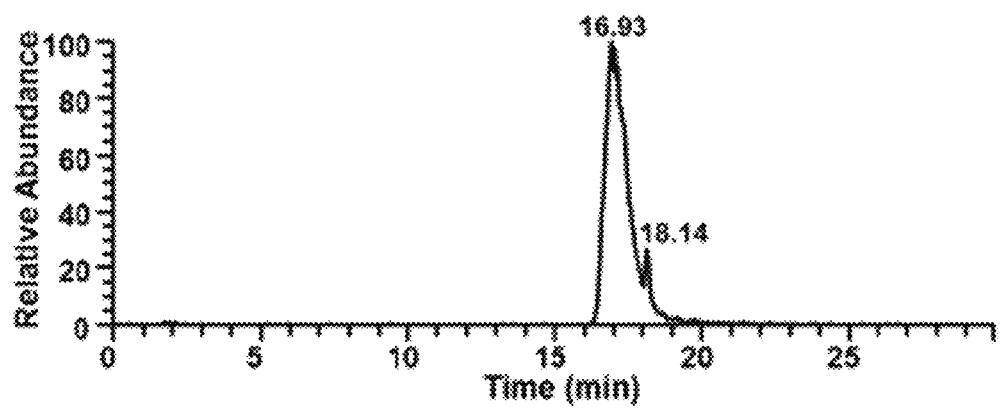
Figure 11B:
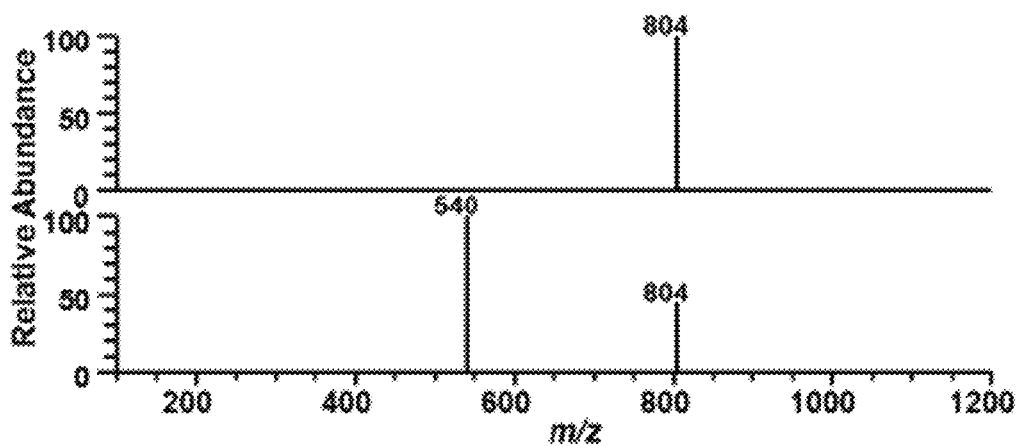

FIG. 11A and FIG. 11B are a set of graphs illustrating the identification of phospholipase A1 activity of MPIaG; Site specificity of MPIaG for OPPC (1-oleoyl-2-palmitoyl-phosphatidylcholine) was determined by LC-MS; (a) The reaction products generated from MPIaG were isolated by HPLC at the time point of 16.93 min (m/z 804, OPPC, upper graph of (B)), and at 18.14 min (m/z 540, 2-palmitoyl-lysophosphatidylcholine, lower graph of (B)).

DESCRIPTION OF THE PREFERRED EMBODIMENTS

The terms used in this invention are defined hereinafter.

The term "recombinant expression vector" used in this invention indicates a vector that is able to express a target protein or target RNA in an appropriate host cell, which is a linear or circular DNA molecule composed of fragments encoding the target polypeptide operably linked to additional fragments provided for the transcription of the expression vector. Such additional fragment includes a promoter and a terminator sequence. The said expression vector includes one or more replication origins, one or more selection markers, and polyadenylation signals, etc. The expression vector is generally induced from a plasmid or virus DNA or contains both of them.

The term "operably linked" used in this invention indicates the functional linkage between a nucleic acid expression regulating sequence and a nucleic acid sequence encoding a target protein or RNA in order to accomplish general functions thereby. For example, the functional linkage between a promoter and a nucleic acid sequence encoding a protein or RNA can affect the expression of the nucleic acid sequence. Operable linking with a recombinant vector can be performed by the genetic recombination technique well-known to those in the art and site-specific DNA cleavage and linkage is accomplished by using an enzyme well known to those in the art.

Hereinafter, the present invention is described in detail.

The present invention provides a polypeptide having both phospholipase and lipase activities and is composed of the amino acid sequence represented by SEQ. ID. NO: 5.

The present invention also provides a polynucleotide encoding the polypeptide having both phospholipase and lipase activities which is represented by SEQ. ID. NO: 5.

The said phospholipase and lipase preferably display excellent activity in pH range of 5~10 and more preferably in pH range of 6~9, and most preferably in pH 8, but not always limited thereto.

The active temperature of the said phospholipase and lipase is preferably 3~30° C., and more preferably 5~25° C., but not always limited thereto.

The polynucleotide herein is preferably composed of the nucleotide sequence represented by SEQ. ID. NO: 3, but not always limited thereto.

In a preferred embodiment of the present invention, DNA was extracted from a tidal flat sediments sample, which was then cloned into a fosmid vector to construct a metagenome library. The library was distributed in a solid nutrient medium supplemented with tricaprylin emulsion, followed by culture. The colonies forming clear zone were screened and the recombinant plasmid pFosPlaG was isolated, followed by nucleotide sequencing. The identified gene (SEQ. ID. NO: 1) was registered at GenBank, USA (Accession Number: EU285670). The open reading frame (ORF) corresponding to the region between $2881^{st}$ and $4578^{th}$ nucleotide of the sequence represented by SEQ. ID. NO: 1 is the protein coding region having both phospholipase and lipase activities, which was identified as the gene having both phospholipase and lipase activities that is composed of the nucleotide sequence represented by SEQ. ID. NO: 2 (1698 bp). The gene having both phospholipase and lipase activities herein was named PlaG.

In a preferred embodiment of the present invention, the phospholipase/lipase PlaG (the protein having both phospholipase and lipase activities) sequence of the present invention was compared with other conventional proteins using BLAST database. As a result, the protein displayed homology in the amino-terminal and carboxy-terminal of the total sequence with other proteins having different characteristics. Particularly, 287 amino acid residues of the amino-terminal showed the highest homology with a Beggiatoa sp. PS derived secreted protein (ZP_02001945), which was as high as 54% (see FIG. 1A). In the meantime, 167 amino acid residues of the carboxy-terminal displayed the highest homology with Grimontia hollisae CIP 101886 derived phospholipase, but showed low homology with the previously reported phospholipase gene group, which was as low as 30~35%, suggesting that the gene of the present invention was a novel gene encoding lipolytic enzyme. The homology in amino acid sequence was compared between the phospholipase/lipase PlaG of the present invention and the homologous phospholipases. As a result, it was confirmed that the sequence of the invention had a catalytic triad composed of $435^{th}$ Ser, $496^{th}$ Asp, and $560^{th}$ His and the conservative Gly-X-Ser-X-Gly motif of α/β hydrolase, and the surrounding amino acids were composed of characteristic sequences of phospholipase A (see FIG. 1B). In particular, 26 amino acid residues in the amino-terminal were identified as a secreted signal peptide and the sequence range from the $27^{th}$ residue (Ala) where the secreted signal peptide ends to the $157^{th}$ residue (Gly) repeated as following range between the $158^{th}$ Thr and the $287^{th}$ Gly. That is, the gene represented by SEQ. ID. NO: 2 was confirmed to have the structure composed of the unknown functional domain made of 287 amino acid residues of the amino-terminal and the functional domain (MPIaG) composed of 278 amino acids of the carboxy-terminal. Based on the founding, the open reading frame MPIaG composed of only the catalytic domain was designed by using the sequence represented by SEQ. ID. NO: 2, which was then represented by SEQ. ID. NO: 3. Lipase is generally apt to be secreted extracellularly and this process differs from a type of microorganism. So, the open reading frame design herein is to avoid such difficulty of the exogenous protein expression. Guanine-cytosine content in the MPIaG gene having both phospholipase and lipase activities and represented by SEQ. ID. NO: 3 was 44.1%, molecular weight of the protein obtained therefrom was approximately 30.5 kDa, and isoelectric point (pI) was 4.0.

In a preferred embodiment of the present invention, a phylogenetic tree was constructed using the amino acid sequence (SEQ. ID. NO: 5) of the polypeptide phospholipase/lipase MPIaG (the protein having both phospholipase and lipase activities) encoded by the sequence represented by SEQ. ID. NO: 3 along with other amino acid sequences of various lipases and phospholipases known so far. As a result, the phospholipase/lipase MPIaG of the present invention did not belong to any lipase family but had higher correlation with rather phospholipase in phylogenetically (see FIG. 3). That is, the phospholipase/lipase MPIaG originated from tidal flat metagenome of the present invention had a common sequence shared with lipase or phospholipase A but was definitely a novel enzyme displaying low homology with the conventional lipase or phospholipase.

In a preferred embodiment of the present invention, the MPIaG gene represented by SEQ. ID. NO: 3 was cloned into a vector (see FIG. 2), and E. coli was transfected with the vector. The phospholipase/lipase MPIaG produced from the transformant was confirmed by SDS-PAGE. The confirmed gene had the molecular weight of approximately 31 kDa. The phospholipase/lipase MPIaG of the present invention was also confirmed to express in a water-soluble form (see FIG. 10).

In a preferred embodiment of the present invention, the phospholipase/lipase MPIaG of the present invention was dropped on the solid medium supplemented with phosphatydilcholine emulsion to investigate phospholipase activity of the MPIaG gene represented by SEQ. ID. NO: 3. The activity was measured by investigating the clear zone formed therein. As a result, the clear zone was clearly formed on the solid medium treated with the phospholipase/lipase MPIaG of the present invention, suggesting that the MPIaG gene had phospholipase activity as well (see FIG. 4).

The phospholipase/lipase MPIaG of the present invention is characterized by followings: it is stable in the pH range of 5~10 and displays maximum activity at pH 8 (see FIG. 5); it is active at the temperature of up to 40° C. and shows maximum activity at 25° C. (see FIG. 6); and it has the melting temperature of 38.5° C. which has been confirmed by differential scanning calorimetry (DSC) (see FIG. 7). Specificity of the phospholipase/lipase MPIaG of the present invention to various phospholipids was investigated. As a result, it showed excellent activity to phosphatydilcholine, phosphatydilethanolamine, and phosphatydilglycerol, but did not decompose phosphatydilserine and phosphatydil acid known to be degraded by secretory phospholipase A (see FIG. 8). MPIaG demonstrated high preference to para-nitrophenyl ester having long acyl straight chain, triglyceride having short acyl straight chain, and phospholipid having medium length acyl straight chain, suggesting that it has broad chain length specificity over substrate. The purified enzyme demonstrated its activity to triolein (C18:1) not hydrolyzed by esterases. Hydrolase activity of the purified enzyme with increasing concentrations of tributyrin was measured and as a result the enzyme showed interfacial activity, indicating MPIaG was not an esterase (see FIG. 9A). In addition, hydrolysis site of MPIaG was determined by liquid chromatography mass spectrometry (LC-MS) using 1-oleoly-2-palmitoyl-phosphatidylcholine (OPPC) (see FIG. 11). Particularly, MPIaG was reacted with OPPC (molecular weight: 759) at 25° C. for 12 hours, followed by LC-MS. LC-MS result confirmed that MPIaG decomposed OPPC (m/z 804, [M-H+HCOOH]$^-$) to produce the reaction product (m/z 540). If MPIaG digested palmitic acid at sn-2 site of OPPC, the reaction product would have been observed at m/z 567. However, MS spectrum was detected at m/z 540 corresponding to 2-palmitoyl-lysophosphatidylcholine. Therefore, it was suggested that MPIaG could be identified as phospholipase A1 that is able to accelerate hydrolysis of acyl group in sn-1 site of phospholipid. In addition, it was also investigated how the enzyme could be affected by various additives. As a result, the enzyme activity was approximately 10 times increased by $Ca^{2+}$ (see Table 1) and the activity was not inhibited by various organic solvents (see Table 2).

The amino acid variants or fragments having different sequences from that of the polypeptide of the present invention having the amino acid sequence represented by SEQ. ID. NO: 5, which can be generated by deletion, insertion, substitution, or combination of amino acid residues of the polypeptide, can also be included in the criteria of the present invention as long as the variants or the fragments do not affect the function of the protein. It is well known to those in the art that the modification of amino acid in protein and peptide is acceptable as long as it does not change the general activity of molecule. Such modification includes phosphorylation, sulfation, acrylation, glycosylation, methylation, and farnesylation. Therefore, the present invention includes not only the polypeptide having the amino acid sequence represented by SEQ. ID. NO: 5 but also the polypeptide having the same amino acid sequence and a variant thereof or an active fragment thereof. Herein, the polypeptide having the same amino acid sequence indicates that it has at least 80% homology in amino acid sequence, more preferably at least 90%, and most preferably at least 95% homology, but not always limited thereto and actually the sequence having at least 70% homology in amino acid sequence and showing the same biochemical activity can be included in this invention.

The polynucleotide of the present invention is preferably the one represented by SEQ. ID. NO: 3. However, considering codon degeneracy or preference of codon in a living thing which is supposed to express the gene having both phospholipase and lipase activities, various modification or transformation in the coding region is allowed as long as the modification or the transformation does not make any change in amino acid sequence of the protein having both phospholipase and lipase activities expressed from the coding region. Such modification or transformation can also be allowed in other regions than the coding region as long as the modification or transformation does not affect the gene expression. Such modified genes are also included in the criteria of the present invention, which is well understood by those in the art. Therefore, the present invention includes the polynucleotide actually having the same nucleotide sequence as the gene represented by SEQ. ID. NO: 3 having both phospholipase and lipase activities and the fragments thereof. The "polynucleotide actually having the same nucleotide sequence" means the polynucleotide having at least 80% homology, more preferably at least 90% homology, and most preferably at least 95% homology in sequence, but not always limited thereto. In fact, the polynucleotide having at least 70% homology in sequence and having the same biochemical activity to the protein encoded is included in this invention as well. As explained hereinbefore, the polynucleotide of the present invention is allowed to have substitution, deletion, insertion, or combination of one or more nucleic acid nucleotides, suggesting that it can be modified, as long as the modified polynucleotide still can encode a protein having the same activity. Such modified polynucleotide can also be included in the criteria of the present invention. The polypeptide having the amino acid sequence represented by SEQ. ID. NO: 5 is preferably encoded by the nucleic acid molecule having the polynucleotide sequence represented by SEQ. ID. NO: 3, but not always limited thereto. In fact, the polypeptide of the present invention can also be encoded by any nucleic acid molecule that has the nucleotide sequence whose sequence is different but is alike to the sequence represented by SEQ. ID. NO: 3 as long as it can encode the protein of the present invention. The nucleic acid molecule sequence can be single-stranded or double-stranded DNA or RNA (mRNA).

The present invention also provides a recombinant expression vector comprising the polynucleotide of the present invention represented by SEQ. ID. NO: 3.

In the course of the construction of the recombinant expression vector, expression regulating sequences such as promoter, terminator or enhancer and sequences for membrane targeting or secretion are properly selected according to the type of host to produce the gene or protein having both phospholipase and lipase activities and those sequences can be combined properly according to the purpose of use.

The expression vector of the present invention includes plasmid vector, cosmid vector, bacteriophage vector, and virus vector, but not always limited thereto. The expression vector can be constructed to meet the purpose of use by containing an expression regulating element such as promoter, operator, initiation codon, stop codon, polyadenylation signal and enhancer, a signal sequence for membrane targeting or secretion, or a leader sequence. The promoter of the expression vector can be constitutive or inductive. When the host is *Escherichia* sp., the signal sequence can be PhoA signal sequence or OmpA signal sequence. When the host is *Bacillus* sp., the signal sequence can be α-amylase signal sequence or subtilisin signal sequence. When the host is yeast, the signal sequence can be MFα signal sequence or SUC2 signal sequence. When the host is an animal cell, the signal sequence can be insulin signal sequence, α-interferon signal sequence, or antibody molecule signal sequence, but not always limited thereto. The expression vector can include a selection marker for the selection of a host cell appropriate for harboring an expression vector. If the expression vector is replicable, it can contain a replication origin. When the recombinant expression vector containing the gene encoding the phospholipase/lipase MPIaG of the present invention is introduced in a host and the phospholipase/lipase MPIaG protein is expressed therein, the protein activity can be observed. Therefore, the transformed host cell can be selected without a selection marker by adding a substrate such as tricaprylin to the culture medium of the host cell.

The recombinant expression vector of the present invention can contain the sequence appropriate for the purification of the expressed target. Particularly, the polynucleotide encoding the tag for separation and purification operably linked to the gene having both phospholipase and lipase activities can be linked to the vector. At this time, the tag for separation and purification is selected from the group consisting of GST, poly-Arg, FLAG, His-tag, and c-myc, or two or more of those tags can be linked stepwise.

In a preferred embodiment of the present invention, His-tag is linked to C-terminal, and then the expressed phospholipase/lipase MPIaG was purified by using Ni-NTA (Ni-nitriloteiacetic acid, Qiagen, Germany) column.

In a preferred embodiment of the present invention, the MPIaG gene represented by SEQ. ID. NO: 3 was cloned in a vector (see FIG. 2), and *E. coli* was transfected with the vector. Then, the phospholipase/lipase MPIaG protein produced from the transformant was confirmed by SDS-PAGE. As a result, it was confirmed that the protein having the molecular weight of approximately 31 kDa was successfully produced. It was also confirmed that the phospholipase/lipase MPIaG of the present invention was expressed in a water-soluble form (see FIG. 10).

The present invention also provides a transformant prepared by transfecting a host cell with the recombinant expression vector comprising the polynucleotide of the present invention represented by SEQ. ID. NO: 3.

After inserting the recombinant expression vector of the invention in a proper host cell, for example *E. coli* or yeast, preferably *E. coli*, the transfected host cell was cultured to replicate or mass-produce DNA of the novel gene or the novel protein having both phospholipase and lipase activities. Culture method, medium and conditions can be selected by those in the art based on the conventional methods and conditions well known to those in the art.

In a preferred embodiment of the present invention, the recombinant vector pET22b(+)-MPIaG containing the novel MPIaG gene was constructed (see FIG. 2), which was inserted in *E. coli* BL21(DE3). The activity of the phospholipase/lipase MPIaG expressed in the transfected strain was investigated. As a result, *E. coli* transfected with the pET-22b(+) vector that did not contain the said gene did not degrade tricaprylin and phosphatidylcholine. On the contrary, *E. coli* transfected with the vector containing the phospholipase/lipase MPIaG of the present invention degraded tricaprylin and phosphatidylcholine successfully, and thus showed both phospholipase and lipase activities (see FIG. 4). Accordingly, it was confirmed that the gene having both phospholipase and lipase activities of the present invention which had been isolated from the metagenome library of tidal flat sediments was expressed in the *E. coli* transformant and displayed its activity effectively therein. To confirm both phospholipase and lipase activities, an equal amount of the protein was loaded on the solid medium containing tricaprylin and phosphatidylcholine. As a result, clear zone was formed on the medium containing tricaprylin (lipase substrate) and phosphatydilcholine (phospholipid), suggesting that not only phospholipase activity but also lipase activity was displayed (see FIG. 4). The *E. coli* transformant BL21(DE3)/pET22b(+)-MPIaG was deposited under the Budapest Treaty at Korean Collection for Type Cultures (KCTC), Korea Research Institute of Bioscience and Biotechnology (KRIBB) on May 30, 2011 (Accession No: KCTC 11942BP). The transformant will be irrevocably and without restriction or condition released to the public upon issuance of a patent.

The present invention also provides a preparation method of a recombinant protein having both phospholipase and lipase activities which comprises the following steps:

1) constructing a recombinant expression vector containing the polynucleotide SEQ. ID. NO: 3;

2) preparing a transformant by introducing the recombinant expression vector above into a host cell; and, 3) culturing the transformant and inducing the expression of the recombinant protein therein, followed by obtaining the expressed recombinant protein.

In step 1), the polynucleotide encoding the tag for separation and purification and the protease recognition site can be additionally linked to N-terminal of the polynucleotide. Thus, it is possible to obtain the purified or the original form of phospholipase/lipase MPIaG. That is, the original form of phospholipase/lipase MPIaG can be obtained by addition of the additional step of purifying the phospholipase/lipase MPIaG by using the tag for separation and purification and then treating a protease capable of digesting the protease recognition site thereto.

The tag for separation and purification is preferably one or more tags selected from the group consisting of GST, poly-Arg, FLAG, His-tag, and c-myc, and more preferably His-tag, but not always limited thereto.

The present invention also provides a detergent additive containing the polypeptide comprising the amino acid sequence represented by SEQ. ID. NO: 5 and having both phospholipase and lipase activities as an active ingredient.

The present invention also provides a washing method including the step of treating the surface of a material with the polypeptide of the invention having both phospholipase and lipase activities.

In addition, the present invention provides a use of the polypeptide of the invention having both phospholipase and lipase activities for the preparation of a detergent.

The novel gene isolated from the metagenome library of tidal flat sediments and the protein having phospholipase and lipase activities encoded from the novel gene: are expressed in a water-soluble form to be mass-producible; enable ultra high-purity protein to be obtained through single step purification using an Ni-NTA column; show good activity in the pH range of 5~10; maintain good low temperature activity and stability up to a temperature of 3° C. to 40° C.; and have high resistance against various organic solvents. Therefore, the novel gene and the protein can be usefully used for various industrial fields such as the purification and conversion of oil and fat, bio-medicine, and fine chemistry.

Practical and presently preferred embodiments of the present invention are illustrative as shown in the following Examples, Experimental Examples and Manufacturing Examples.

However, it will be appreciated that those skilled in the art, on consideration of this disclosure, may make modifications and improvements within the spirit and scope of the present invention.

Example 1

Construction of Metagenome Library 10 g of a soil sample collected in tidal flat of Saemangeum reclaimed land, Buan-gun, Jeollabuk-do, Korea was suspended in the equal volume of DNA extraction buffer containing 50 μg/ml of proteinase K [100 mM Tris-HCl (pH 8), 100 mM EDTA (ethylenediaminetetraacetic acid, Sigma, USA), 100 mM sodium phosphate (pH 8, Sigma, USA), 1.5 M NaCl (Junsei, Japan), 1% (w/v) CTAB (hexadecyl trimethyl ammonium bromide, Sigma, USA)], to which an anionic surfactant (sodium dodecyl sulfate, SDS, Sigma, USA) was added at the final concentration of 2% (v/v), followed by reaction at 65° C. for 2 hours. The supernatant was obtained by centrifugation, to which 30% (v/v) polyethylene glycol containing 1.6 M NaCl was added at the equal volume, followed by well-mixing. The precipitated DNA was isolated by centrifugation, which was then suspended in TE buffer. The equal volume of phenol/chloroform/isoamyl alcohol (25:24:1) and chloroform/isoamyl alcohol (24:1) mixed solution was added thereto, followed by extraction twice. The supernatant was obtained by centrifugation, to which isopropanol was added to precipitate DNA. The precipitated DNA was completely dried and then dissolved in sterilized water. After eliminating impurities, electrophoresis was performed using PFGE (pulse-field gel electrophoresis) to digest the DNA into 23~48 kb fragments. Gel elution was performed using Gelase (Epicentre, USA). The purified DNA fragments were used to construct a metagenome library by using CopyControl fosmid library construction kit (Epicentre, USA).

To examine the quality of the library, transformants were selected randomly and recombinant plasmids were extracted therefrom, which were treated with selected restriction enzyme. As a result, they all contained recombinant plasmid and the average size of the inserted metagenome was 35 kb.

Example 2

Screening and Isolation of the Recombinant Plasmid Having Lipase Activity

To screen a gene having lipase activity from the metagenome library constructed in Example 1, the metagenome library was cultured on a solid medium containing emulsified tricaprylin.

Particularly, the said metagenome library was distributed on a solid nutritive medium [1% (w/v) trypton, 0.5% (w/v) yeast extract, 0.5% (w/v) NaCl, 1.5% (w/v) agar] supplemented with tricapryline emulsion [1% (v/v) tricaprylin, 1 mM $CaCl_2$, 0.5% (w/v) Gum arabic], followed by culture at 37° C. When tricaprylin is decomposed by lipase, clear zone is formed. So, the colonies forming such clear zone were selected. The recombinant plasmid was isolated from such colonies showing excellent activity of decomposing tricaprylin and named pFosPlaG.

Example 3

Sequencing of the Recombinant Plasmid Having Excellent Lipase Activity

<3-1> Sequencing of Recombinant Plasmid

Sequencing of the recombinant plasmid pFosPlaG isolated from the metagenome library was performed by shotgun sequencing.

Particularly, DNA fragments were prepared physically by using pipetting from pFosPlaG, which were sub-cloned in pUC118 (TaKaRa) vector. Sequencing was performed using an automatic sequencer (ABI 3730 DNA analyzer).

As a result, the pFosPlaG was in the size of 28,845 bp and the nucleotide sequence of the gene was the same as the sequence represented by SEQ. ID. NO: 1, which was registered at Gen Bank, USA, under the accession number of EU285670. Only those ORFs (open reading frames) that have the e-value under $e^{-2}$ were identified by using National Center for Biotechnology Information (NCBI) ORF finder. The function of each ORF was predicted by using BlastX and the NCBI Conserved Domain Database (CDD).

Figure 1A:
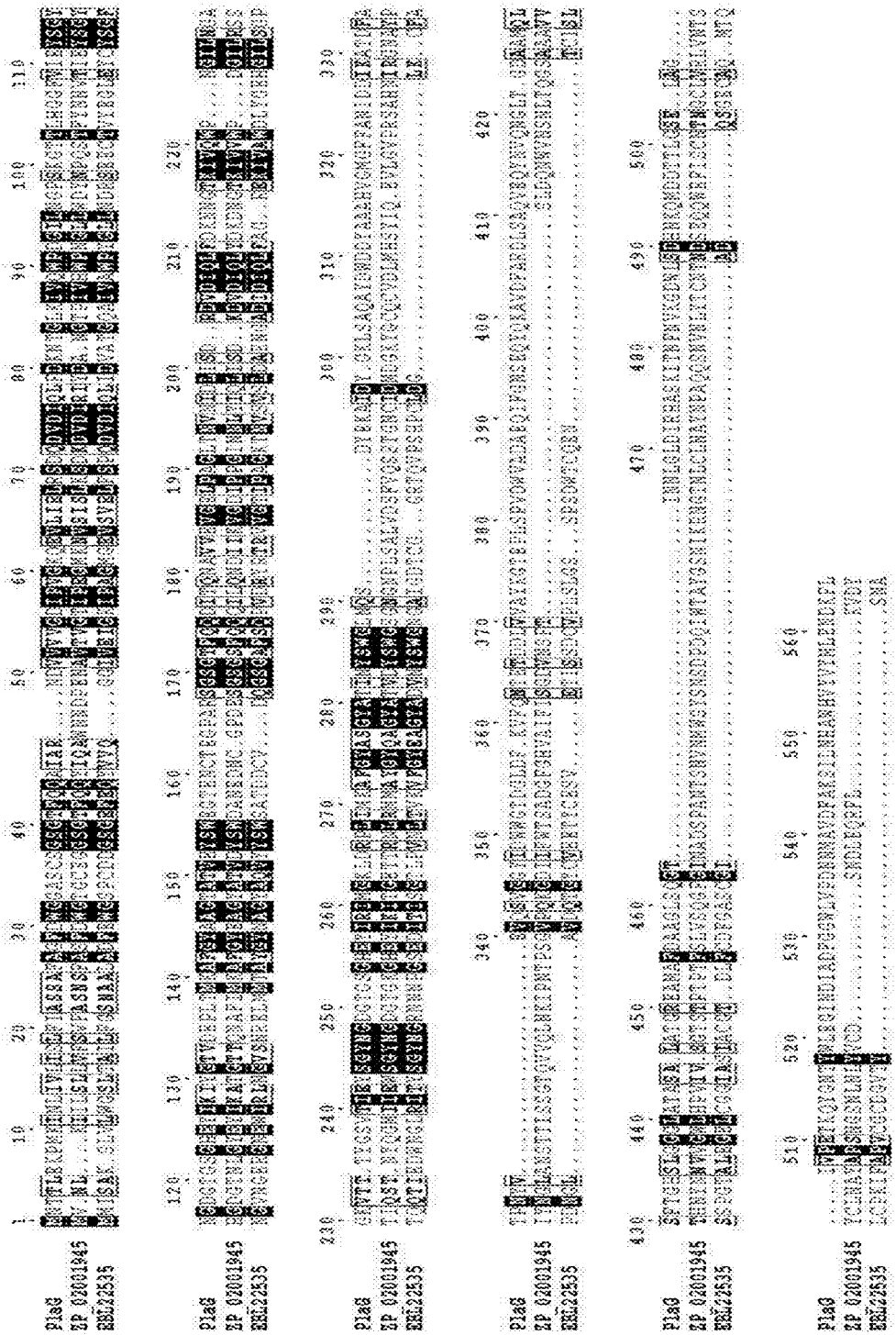
FIG. 1A and FIG. 1B show homology among the phospholipase/lipase PlaG (the protein PlaG having both phospholipase and lipase activities) of the present invention, the protein having similarity to amino-terminal (A) thereof, and the protein having similarity to carboxy-terminal (B)
Figure 1B:
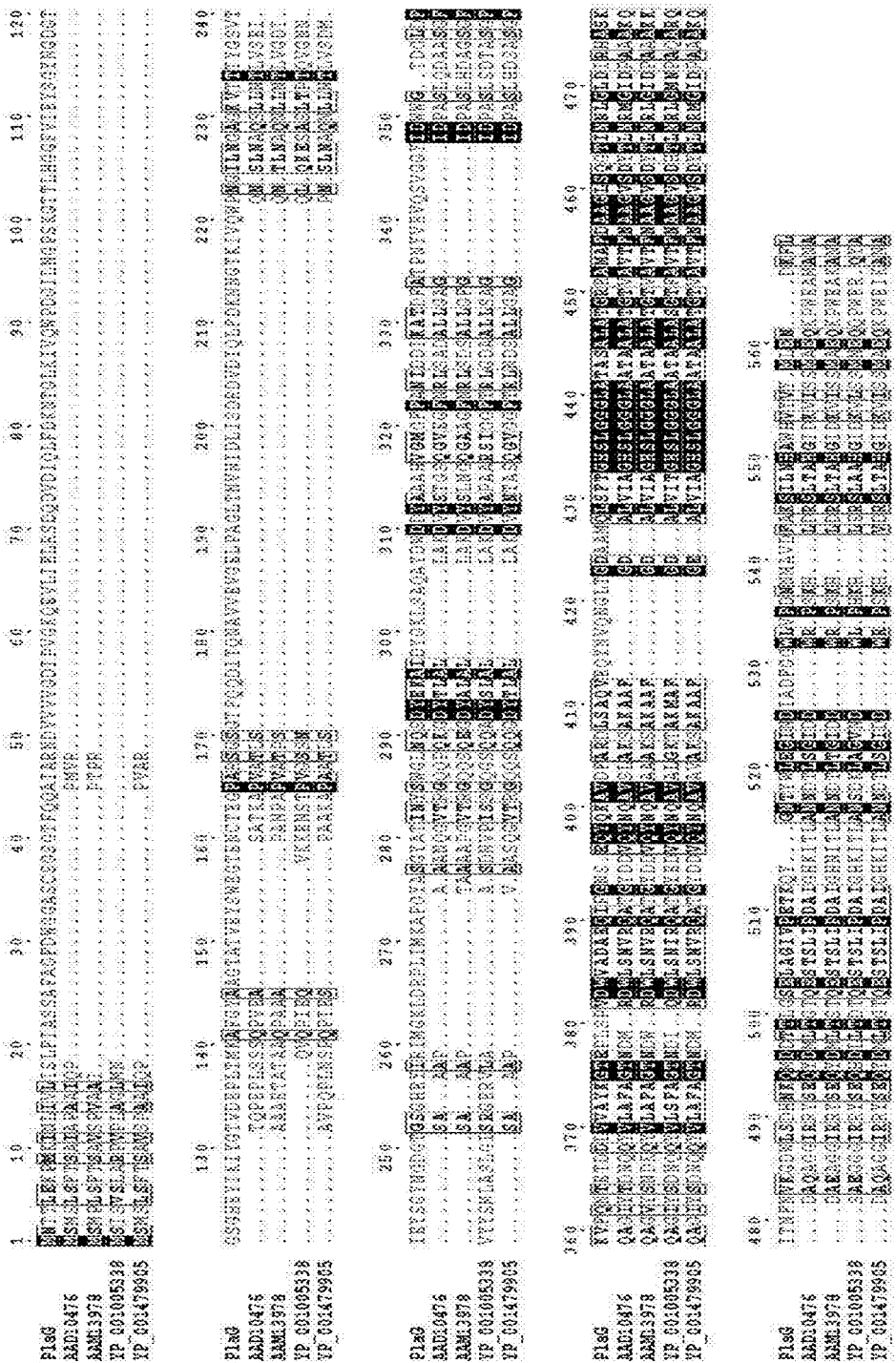

As a result, as shown in Table 1, total 15 ORFs were identified. The ORF corresponding to the region from the nucleotide #2881 to #4578 in the nucleotide sequence complementary to the sequence represented by SEQ. ID. NO: 1 was confirmed to be phospholipase protein coding region. So, the gene was named plaG. The gene (plaG) having both phospholipase and lipase activities of the present invention was composed of 1698 nucleotides and GC content was 44.94%. The phospholipase/lipase PlaG (the protein PlaG having both phospholipase and lipase activities; SEQ. ID. NO: 4) expressed from the gene was composed of 566 amino acids, which was identified to be the protein having the molecular weight of approximately 61,187 Da and having both phospholipase and lipase activities.

a novel gene encoding phospholipase. The homology between the amino acid sequence of the phospholipase/lipase PlaG of the present invention and the amino acid sequence of the similar phospholipase was investigated. As a result, it was confirmed that the sequence of the invention had a catalytic triad composed of $435^{th}$ Ser, $496^{th}$ Asp, and $560^{th}$ His and consensus Gly-X-Ser-X-Gly motif of α/β hydrolase, and the surrounding amino acids were composed of characteristic sequences of phospholipase A ([LIV]-{KG}-[LIVFY]-[LIVMST]-G-[HYWV]-S-{YAG}-G-[GSTAC]) (FIG. 1B). In the meantime, 287 amino acid residues in amino-terminal of the phospholipase/lipase PlaG displayed the highest homology (54%) with *Beggiatoa* sp.

TABLE 1

| ORF no. | Length (a.a.) | G + C (%) | Most homologous protein | Putative source organism | Homology (%) | E-value |
|---|---|---|---|---|---|---|
| 1 | 291 | 36.87 | RNA polymerase sigma factor | *Planctomyces maris* DSM 8797 | 39 | $2e^{-53}$ |
| 2 | 565 | 44.94 | Phospholipase A | *Grimontia hollisae* CIP 101886 | 31 | $5e^{-06}$ |
| 3 | 334 | 47.56 | NADP-dependent oxidoreductases | *Moritella* sp. PE36 | 88 | $4e^{-173}$ |
| 4 | 208 | 44.34 | hypoxanthine phosphoribosyl-transferase | *Desulfotalea psychrophila* LSv54 | 71 | $2e^{-66}$ |
| 5 | 90 | 37.36 | Putative regulatory protein | *Dictyoglomus thermophilum* H-6-12 | 57 | $8e^{-08}$ |
| 6 | 160 | 33.54 | hypothetical protein | *Pelobacter carbinolicus* DSM 2380 | 49 | $2e^{-26}$ |
| 7 | 328 | 36.58 | Amino acid ABC transporter periplasmic protein | *Hahella chejuensis* KCTC 2396 | 41 | $2e^{-47}$ |
| 8 | 274 | 40.48 | Putative transposase | *Solibacter usitatus* Ellin6076 | 39 | $3e^{-44}$ |
| 9 | 158 | 46.12 | hypothetical protein | *Methanosarcina barkeri* str. Fusaro | 44 | $2e^{-37}$ |
| 10 | 107 | 38.58 | hypothetical protein | *Chlorobium chlorochromatii* CaD3 | 61 | $4e^{-36}$ |
| 11 | 1095 | 35.92 | transcriptional regulator | *Bacillus* sp. SG-1 | 22 | $5e^{-57}$ |
| 12 | 253 | 39.76 | NAD(P)H dehydrogenase | *Desulfatibacillum alkenivorans* AK-01 | 37 | $4e^{-43}$ |
| 13 | 114 | 31.59 | Transposase | *Pseudomonas aeruginosa* | 28 | $1e^{-2}$ |
| 14 | 435 | 34.79 | Hypothetical exported 24-amino acid repeat protein | *Fusobacterium nucleatum* subsp. *vinventii* ATCC 49256 | 32 | $2e^{-44}$ |
| 15 | 308 | 35.38 | Transposase | *Marinobacter* sp. ELB17 | 25 | $2e^{-11}$ |

<3-2> Homology Analysis

The amino acid sequence was compared between the protein of the invention and the conventional proteins using BLAST database.

As a result, the phospholipase/lipase MPaIG (the protein having both phospholipase and lipase activities; SEQ. ID. NO: 5) expressed from the phospholipase/lipase PlaG (SEQ. ID. NO: 4), more preferably from the catalytic domain MPIaG of the PlaG, demonstrated the highest homology with *Grimontia hollisae* CIP 101886 but showed low homology with the previously reported phospholipase gene group, which was as low as 30~35%, suggesting that the gene was PS derived secreted protein (ZP_02001945) (FIG. 1A). In particular, 26 amino acid residues in the amino-terminal were identified as a secreted signal peptide and the sequence range from the $27^{th}$ residue (Ala) where the secreted signal peptide ends to the $157^{th}$ residue (Gly) repeated as following range between the $158^{th}$ Thr and the $287^{th}$ Gly (FIG. 3). Based on the presence of the secreted signal peptide and the repeated sequence and the result of BLAST database searching, it was predicted that the phospholipase/lipase PlaG is composed of an unknown functional domain and a catalytic domain. The functional domain of the phospholipase/lipase PlaG was named phospholipase/lipase MPIaG.

<3-3> Phylogenetic Analysis

A phylogenetic tree was constructed using the amino acid sequence (SEQ. ID. NO: 5) of the phospholipase/lipase MPIaG along with other amino acid sequences of various lipases and phospholipases known so far.

As a result, as shown in FIG. 3, the phospholipase/lipase MPIaG of the present invention did not belong to any lipase family but had higher correlation with rather phospholipase phylogenetically (FIG. 3). Moreover, the phospholipase/lipase MPIaG of the present invention was far apart from *Staphylococcus hyicus* originated lipase known to have not only lipase activity but also excellent phospholipase activity. The conventional *Serratia* sp. MK1, *Serratia marcescens*, *Yersinia enterocolitica* 8081, and *Serratia proteamaculans* 568 derived phospholipase amino acid sequences demonstrated high homology (59.7~88.1%) with each other, but showed low homology with that of the phospholipase/lipase MPIaG of the present invention (17.2~20.4%). That is, the phospholipase/lipase MPIaG originated from tidal flat metagenome of the present invention had a common sequence shared with lipase or phospholipase A but was definitely a novel enzyme displaying low homology with the conventional lipase or phospholipase.

Example 4

Construction of Transformant

To construct a recombinant plasmid capable of producing the novel phospholipase/lipase MPIaG of the present invention in a large scale, ORF composed of only PlaG catalytic domain (MPIaG) was designed and prepared thereby. The product [837 bp (SEQ. ID. NO: 3) from the $862^{nd}$ bp of the sequence represented by SEQ. ID. NO: 2] was cloned in the restriction enzyme site (Ndel and Xhol) of pET-22b(+) (Novagen) vector. *E. coli* BL21(DE3)/pET22b(+)-MPIaG was constructed by transfecting *E. coli* BL21(DE3) with the prepared recombinant vector.

Particularly, polymerase chain reaction (PCR) was performed by using the recombinant plasmid pFosPlaG screened from the metagenome library as template DNA with the synthesized N-terminal primer represented by SEQ. ID. NO: 6 and the synthesized C-terminal primer represented by SEQ. ID. NO: 7.

```
SEQ. ID. NO: 6:
5'-CCCCATATGTTAAATCAGTCTGATTATGA-3'

SEQ. ID. NO: 7:
5'-CCCCTCGAGAAATTTATCGTTCTCAAGCAT-3'
```

The N-terminal primer and the C-terminal primer of the MPIaG gene of the present invention have Ndel and Xhol cleavage site, respectively, and are oligonucleotides represented by SEQ. ID. NO: 6 and SEQ. ID. NO: 7 respectively. The recombinant vector pET22b(+)-MPIaG contains a very powerful T7 promoter and a read signal therein. When this vector is introduced in such a host as *E. coli* BL21(DE3) containing T7 RNA polymerase, the phospholipase/lipase MPIaG can be mass-produced therefrom. Also, a tag encoding 6 histidines playing a role in purification of phospholipase and lipase is formed in the C-terminal.

The DNA fragments amplified massively through PCR were digested with Ndel and Xhol, which were then ligated to the expression vector pET-22b(+) treated with the same restriction enzymes and calf intestinal phosphatase to construct the recombinant plasmid pET22b(+)-MPIaG for the expression of phospholipase and lipase (FIG. 2). A transformant was constructed by transfecting *E. coli* BL21(DE3) with the recombinant plasmid pET22b(+)-MPIaG through electroporation. The constructed transformant was named *E. coli* BL21(DE3)/pET22b(+)-MPIaG, which was deposited at Korean Collection for Type Cultures (KCTC), Korea Research Institute of Bioscience and Biotechnology (KRIBB) on May 30, 2011 (Accession No: KCTC 11942BP).

Example 5

Confirmation of Phospholipase/Lipase MPIaG Production

<5-1> Expression and Purification of Phospholipase/Lipase MPIaG

The *E. coli* BL21(DE3)/pET22b(+)-MPIaG constructed in Example 4 was cultured in a liquid nutritive medium [1% (w/v) trypton, 0.5% (w/v) yeast extract, 0.5% (w/v) NaCl] containing ampicillin (100 μg/ml) until $OD_{600}$ reached 0.6. IPTG (isopropyl-β-D-thiogalactopyranoside) was added to the culture solution (final conc.: 0.5 mM), followed by further culture for 12 hours. *E. coli* BL21(DE3)/pET22b(+)-MPIaG was obtained by centrifugation, which was suspended in binding buffer (50 mM Tris-HCl, pH 8, 500 mM NaCl, 10 mM imidazole). The cell suspension was lysed by ultrasonication. The cell lysate was centrifuged to obtain supernatant. The supernatant was loaded on Ni-NTA (nitriloteiacetic acid) column to elute phospholipase and lipase by imidazole gradient, followed by dialysis-concentration. To confirm the purified phospholipase/lipase MPIaG, SDS-PAGE (sodium dodecyl sulfate-polyacrylamide gel electrophoresis) was performed, followed by staining with Coomassie brilliant blue.

As a result, as shown in FIG. 10, the phospholipase/lipase MPIaG of the present invention was successfully produced as the protein in the molecular weight of approximately 31 kDa after the expression induction. The said molecular weight was very close to the expected molecular weight of the amino acid sequence of the phospholipase/lipase MPIaG of the present invention, suggesting that this protein band was the novel phospholipase/lipase MPIaG of the invention. The phospholipase/lipase MPIaG of the present invention was expressed in a water-soluble form. It was confirmed that the protein expression of the phospholipase/lipase MPIaG of the invention was significantly increased, comparing with the full-length protein phospholipase/lipase PlaG (FIG. 10). In addition, the full-length protein phospholipase/lipase PlaG always existed together with a non-specific protein even after being through various purification processes or being expressed by using a new vector system. On the other hand, the phospholipase/lipase MPIaG of the present invention can be produced with high purity even with one-step purification process using Ni-NTA column.

<5-2> Confirmation of Phospholipase Activity

The recombinant plasmid pFosPlaG derived from the metagenome library was isolated in the solid nutritive medium supplemented with tricaprylin emulsion which has been widely used for the isolation/confirmation of lipase gene. To investigate the phospholipase activity of the gene, the purified phospholipase/lipase MPIaG was loaded on the solid medium supplemented with phosphatydilcholine emulsion [0.5% (w/v) phosphatydilcholine, 0.5% (w/v) taurocholic acid, 20 mM $CaCl_2$], followed by observing clear zone to confirm the activity. As the comparative group, lipase CALB (lipase B from *Candida antarctica*) exhibiting excellent lipase activity and the cell lysate of *E. coli* BL21 (DE3), the host cell used for the construction of a transformant, were used.

As a result, as shown in FIG. 4, the cell lysate of *E. coli* BL21(DE3) did not show the activity on both solid media. CALB formed clear zone only on the solid nutritive supplemented with tricaprylin emulsion, while the gene of the present invention formed clear zone on both solid media, suggesting that the gene of the invention had not only lipase activity but also phospholipase activity (FIG. 4).

Example 6

Characteristics of Phospholipase/Lipase MPIaG Derived from Tidal Flat Metagenome Enzyme activity of the phospholipase/lipase MPIaG purified in Example 5 over temperature and pH, specificity over various substrates with different carbon chain length, and relation of the phospholipase/lipase MPIaG with various metal ions, inhibitors, and organic solvents were investigated based on lipase activity.

Particularly, enzyme activity was measured by the following two methods. First method was pH-stat. 5 ml of triglycerol and 495 ml of gum arabic suspension [20 mM NaCl, 1 mM $CaCl_2$, 0.5% (w/v) gum arabic] were mixed to prepare an emulsion using Waring blender. 25 ml of the prepared triglycerol emulsion was loaded in a reactor equipped with an apparatus of controlling temperature, to which 10 mM NaOH was loaded to regulate pH as 8. The phospholipase/lipase MPIaG enzyme solution purified above was loaded to the emulsion, followed by hydrolysis at 25° C. During the hydrolysis reaction, the amount of NaOH was measured by pH titrator (842T Tirando, Metrohm). 1 unit (U) of enzyme was defined as the enzyme amount capable of producing 1 μmol of fatty acid. The second method was spectrophotometric assay as standard method of the present invention. Particularly, the phospholipase/lipase MPIaG enzyme solution was added to the reaction solution [20 μl of 10 mM para-nitrophenyl ester substrate, 40 μl of ethanol, and 940 μl of 50 mM Tris-HCl (pH 8)], followed by reaction for 5 minutes. The increasing rate of para-nitrophenol hydrolyzed from the substrate was continuously measured at $OD_{405}$. Unless informed otherwise, p-nitrophenyl caprate (C10) was used as a substrate. 1 unit (U) of enzyme was defined as the enzyme amount capable of producing 1 μmol of para-nitrophenol via hydrolysis.

<6-1> Characteristics of Phospholipase/Lipase MPIaG Over Temperature and pH

To investigate the enzyme activity over pH, the activities were measured in different pH buffers. As a result, the maximum activity was observed at pH 8. After staying at different pH for 180 minutes, the remaining activity was measured. As a result, the enzyme activity was maintained stably in the pH range of 5~10 (FIG. 5). Phospholipase and lipase activity over temperature was also investigated. As a result, the maximum activity was observed at 25° C. The enzyme activity was still observed at 5° C. (39% of maximum activity). When the temperature was raised more than the optimum activity temperature above, the activity was decreased rapidly (FIG. 6). In addition, melting temperature was also investigated by using differential scanning calorimetry (DSC). As a result, the melting temperature was 38.5° C. (FIG. 7). The above results indicate that the phospholipase/lipase MPIaG of the present invention was the low-temperature activated alkaline lipolytic enzyme.

<6-2> Specificity of Phospholipase/Lipase MPIaG to Various Phospholipids

To investigate substrate specificity to various phospholipids, the purified phospholipase/lipase MPIaG was added to the solid media respectively supplemented with various phospholipid emulsions. Then, the activity over phospholipid was investigated by comparing the size of clear zone. The phospholipid emulsion was composed of 0.5% (v/v) phospholipid substrate, 0.5% (w/v) taurocholic acid, and 20 mM $CaCl_2$. The substrates used herein were phosphatydilcholine (PC, 99% purity), phosphatidylethanolamine (PE, 97% purity), phosphatidylserine (PS, 97% purity), phosphatidylinositol (PI, 98% purity), phosphatidylglycerol (PG, 99% purity), and phosphatidic acid (PA, 98% purity).

As a result, as shown in FIG. 8, the phospholipase/lipase MPIaG of the present invention demonstrated excellent activity to those substrates, phosphatydilcholine, phosphatidylethanolamine, and phosphatidylglycerol, but did not decompose phosphatidylserine and phosphatidic acid known to be degraded by secreted phospholipase A (FIG. 8).

<6-3> Characteristics of Phospholipase/Lipase MPIaG Over Carbon Length

The activity of MPIaG to hydrolyze triacylglyceride, olive oil, and phosphatidylcholine was measured by titrating free fatty acid using pH titrator (842 Tirando, Metrohm). By adding 10 mM NaOH solution, pH of the substrate emulsion was regulated to 8.0. Then, a proper amount of enzyme solution was added thereto. Excretion rate of fatty acid was measured by using pH titrator for 5 minutes. 1 unit of lipase activity was defined as the enzyme amount capable of releasing 1 μmole of fatty acid. To exclude the non-enzymatic hydrolysis value of the substrates, the activity was measured without enzyme addition for every measurement under different conditions, which would be the control reaction.

As a result, specific enzyme activity of MPIaG toward olive oil and phosphatidylcholine was 2957±144 and 1735±147 $Umg^{-1}$, respectively. MPIaG was a member of phospholipase family, but showed a significant lipase activity to olive oil.

To further investigate specificity to substrate each having different carbon length, pH titration was performed with triacylglycerides such as tributyrin (C4), tricaprylin (C8), tricaprin (C10), trilaurin (C12), tripalmitin (C16), and triolein (C18:1). As a result, the highest enzyme activity was observed to tributyrin (C4) and the enzyme activity was significantly decreased as chain extended (FIG. 9A).

Spectrophotometric assay was also performed at room temperature to investigate the activity of MPIaG to para-nitrophenyl ester with various carbon chain lengths, the synthetic substrate. At this experiment, para-nitrophenyl butyrate (C4), para-nitrophenyl caprylate (C8), para-nitrophenyl caprate (C10), para-nitrophenyl laurate (C12), para-nitrophenyl palmitate (C16), and para-nitrophenyl stearate (C18) were used as substrates for the comparison of the activity. 5 mM $Ca^{2+}$ was added to the reaction solution. The reaction product para-nitrophenol was continuously measured for 5 minutes at $OD_{450}$ using DU800 spectrophotometer (Beckman). To exclude the non-enzymatic hydrolysis value of the substrates, the activity was measured without enzyme for every measurement under different conditions, which would be the control reaction.

As a result, the MPIaG of the present invention demonstrated the highest activity (approximately 112 times) to para-nitrophenyl palmitate (C16) and the second highest activity to para-nitrophenyl butyrate (C4) (FIG. 9B).

Specificity of MPIaG over the location and chain length of phospholipid was investigated. To do so, phosphatydilcholine with different carbon chain lengths (C6, C7, C8, and C14) and 1-oleoly-2-palmitoyl-phosphatidylcholine (OPPC) were used. The purified MPIaG was added to 50 mM tris buffer (pH 8.0) containing 5 mM $CaCl_2$ and 150 mM NaCl, followed by enzyme reaction along with 1 mM substrate for 12 hours at 25° C. The reaction product was analyzed by liquid chromatography mass spectrometry (LC-MS) using Finnigan LCQ. Advantage MAX ion trap mass spectrometer (Thermo Fisher Scientific) was equipped with electrospray ionization source. HPLC isolation was performed with HILIC guard column (4×2.0 mm, Phenomenex) and Kinetex HILIC column (2.6 μm, 2.1×100 mm, Phenomenex). The moving phase A was 10 mM ammonium formate whose pH was regulated as 3.0 with formic acid. The moving phase B was acetonitrile. Gradient elution was performed at the flow rate of 0.2 ml/min as follows: 0~10 min., 10%~40% A (linear gradient); 10~20 min., 70% A (isocratic). Column temperature was room temperature, and the injection volume was 10 μL. Mass spectra were obtained from m/z in the negative ion mode 100~1200 at the maximum ion injection time of 3 microscans and 200 ms.

As a result, the mass spectra were characterized by [M-H]- and [M-H+HCOOH]- in the negative ion mode. Hydrolase activity of phosphatydilcholine to lysophosphatidylcholine was highest to 1,2-Dioctanoyl-phosphatidylcholine (diC8PC) (FIG. 9C). Therefore, MPIaG was confirmed to have high preference to para-nitrophenyl ester having long acyl straight chain, triglyceride having short acyl straight chain, and phospholipid having medium length acyl straight chain, showing that it had broad chain length specificity over substrate. The purified enzyme demonstrated its activity to triolein (C18:1) not hydrolyzed by esterases. Hydrolase activity of the purified enzyme as tributyrin concentration increased was measured and as a result the enzyme showed interfacial activity, indicating MPIaG was not an esterase (FIG. 9A). In addition, hydrolysis site of MPIaG was determined by liquid chromatography mass spectrometry (LC-MS) using 1-oleoly-2-palmitoyl-phosphatidylcholine (OPPC) (FIG. 11). Particularly, MPIaG was reacted with OPPC (molecular weight: 759) at 25° C. for 12 hours, followed by LC-MS. LC-MS result confirmed that MPIaG decomposed OPPC (m/z 804, [M-H+HCOOH]⁻) to produce the reaction product (m/z 540). If MPIaG digested palmitic acid at sn-2 site of OPPC, the reaction product would have been observed at m/z 567. However, MS spectrum was detected at m/z 540 ([M-h+COOH-C18:1]-) corresponding to 2-palmitoyl-lysophosphatidylcholine. So, it was suggested that MPIaG could be identified as phospholipase A1 that is able to accelerate hydrolysis of acyl group in sn-1 site of phospholipid.

The MPIaG of the present invention decomposed triolein not degraded by esterase, and showed interfacial activity as the concentration of tributyrin increased, indicating that it is not phosphoesterase/esterase but phospholipase/lipase.

<6-4> Effect of Phospholipase/Lipase MPIaG on Metal Ions and Inhibitors

Enzyme activities over various metal ions and inhibitors at different concentrations were measured as shown in Table 2.

As a result, as shown in FIG. 7, the activities were increased approximately 10 times by $Ca^{2+}$ but strongly inhibited by EDTA. When 2 mM and 5 mM of calcium ion were added, melting temperature of the phospholipase/lipase MPIaG of the present invention was raised from 38.5° C. to 47.2° C. and 49.2° C. respectively. So, it was expected that the structural stability was increased by calcium ion (FIG. 7).

TABLE 2

|  | Enzyme activity relative value (%) | | |
| --- | --- | --- | --- |
| Metal ions and inhibitors | 1 mM | 5 mM | 10 mM |
| $CaCl_2$ | 466 | 1015 | 994 |
| $CuCl_2$ | 135 | 32 | 11 |
| $MgCl_2$ | 105 | 198 | 142 |
| $FeSO_4$ | 137 | 142 | 151 |
| $ZnCl_2$ | 107 | 9 | 5 |
| $NiCl_2$ | 62 | 23 | 7 |
| $CoCl_2$ | 120 | 177 | 116 |
| EDTA (ehylenediaminetetraacetic acid) | 78 | 0 | 0 |
| PMSF (phenyl methyl sulfonyl fluoride) | 94 | 107 | 105 |
| DTT (dithiothreitol) | 93 | 107 | 105 |
| 2-mercaptoethanol | 105 | 108 | 80 |

<6-5> Enzyme Activity of Phospholipase/Lipase MPIaG Over Organic Solvents

To investigate stability of the phospholipase/lipase MPIaG of the present invention against dimethyl sulfoxide (DMSO), dimethylformamide (DMF), 2-propanol, ethanol, methanol, acetonitrile, and acetone shown in Table 3, enzyme activity of the phospholipase/lipase MPIaG was measured at different concentrations of the solvents.

As a result, enzyme activity of the phospholipase/lipase MPIaG was hardly inhibited by those organic solvents at the concentrations of up to 60% (v/v), suggesting that this enzyme would be fully usable in the organic solvent condition in the industry.

TABLE 3

|  | Enzyme activity relative value (%) | | | |
| --- | --- | --- | --- | --- |
| Organic solvent | 20% | 30% | 50% | 60% |
| DMSO (dimethyl sulfoxide) | 98 | 97 | 98 | 81 |
| DMF (dimethylformamide) | 99 | 100 | 93 | 98 |
| 2-propanol | 101 | 97 | 96 | 99 |
| Ethanol | 100 | 95 | 94 | 98 |
| Methanol | 100 | 101 | 93 | 98 |
| Acetonitrile | 100 | 99 | 98 | 99 |
| Acetone | 96 | 100 | 96 | 99 |

<6-6> Comparison of Enzyme Activity of Phospholipase/Lipase MPIaG

Specific activity was compared among the phospholipase/lipase MPIaG of the present invention and CALB (lipase from *Candida antartica*) and CRL (lipase from *Candida rugosa*) by pH-stat.

As a result, as shown in Table 4, even though CALB displayed the highest enzyme activity to the synthetic substrate tributyrin (C4), the phospholipase/lipase MPIaG of the present invention showed the highest enzyme activity to the natural substrate olive oil. Only the phospholipase/lipase MPIaG of the invention showed enzyme activity to the phospholipase substrate phosphatidylcholine. That is, unlike those lipases CALB and CRL, the phospholipase/lipase MPIaG of the invention had phospholipase activity, confirmed quantitatively. In the meantime, considering that *P. pseudoalcaligene* derived lipase demonstrated 5.7 U/mg of phospholipase activity, and Lecitase™ (Novozyme) showed 6 U/mg of phospholipase activity, reported in a research paper (Biochimica et Biophysica Acta 1259 (1995) 9-17), the phospholipase/lipase MPlaG of the present invention characteristically demonstrated excellent lipase activity and phospholipase activity (Table 4).

In addition, specific activity of the phospholipase/lipase MPlaG of the invention and the full-length protein was also investigated using synthetic substrate. As a result, the phospholipase/lipase MPlaG of the invention displayed at least two times increased specific activity, compared to the full-length phospholipase/lipase PlaG.

TABLE 4

|  | Substrates | | |
| --- | --- | --- | --- |
|  | Tributyrin (C4) | Olive oil | phosphatydilcholine |
| Phospholipase/lipase MPlaG of the invention | 140 ± 6.4 | 114.8 ± 11.3 | 13.4 ± 1.5 |

TABLE 4-continued

|  | Substrates | | |
| --- | --- | --- | --- |
|  | Tributyrin (C4) | Olive oil | phosphatydilcholine |
| CALB (lipase from *Candida antartica*) | 294.2 ± 14.5 | 15.3 ± 0.1 | a |
| CRL (lipase from *Candida rugosa*) | 20.3 ± 0.5 | 53.7 ± 1.5 | a | a: not determined

Those skilled in the art will appreciate that the conceptions and specific embodiments disclosed in the foregoing description may be readily utilized as a basis for modifying or designing other embodiments for carrying out the same purposes of the present invention. Those skilled in the art will also appreciate that such equivalent embodiments do not depart from the spirit and scope of the invention as set forth in the appended Claims.

What is claimed is:

1. A washing method comprising the step of treating a surface of a material with a composition comprising a polypeptide having both phospholipase and lipase activities, wherein said polypeptide consists of the amino acid sequence represented by SEQ. ID. NO: 5.

2. The washing method according to claim 1, wherein the polypeptide is encoded by polynucleotide comprising the nucleotide sequence represented by SEQ. ID. NO: 3.

3. The washing method according to claim 1, further comprising the following steps prior to the step of treating a surface:
producing a transformant by introducing a recombinant expression vector containing a polynucleotide encoding the polypeptide into a host cell, wherein said polynucleotide comprises the nucleotide sequence represented by SEQ ID NO: 3;
culturing said transformant to produce a polypeptide consisting of the amino acid sequence represented by SEQ ID NO: 5; and
isolating the polypeptide expressed by said cultured transformant.

4. The washing method according to claim 3, wherein the transformant is deposited under the Accession Number of KCTC 11942BP.

5. The washing method according to claim 1, wherein said polypeptide is active in a pH range of 5-10.

* * * * *

SEQUENCE LISTING

<160> NUMBER OF SEQ ID NOS: 7

<210> SEQ ID NO 1
<211> LENGTH: 28845
<212> TYPE: DNA
<213> ORGANISM: Unknown
<220> FEATURE:
<223> OTHER INFORMATION: pFosPlaG

<400> SEQUENCE: 1

```
ctaagatttg ctcagttgaa gaatcaattg gtgatattct ttatatcaag cgtaaggatt        60
tagatcattg ccgactcgca cgcgtaccgt atgttttttgg gaaaaccagt tttgctctgc       120
ttgagtgagc gaaacagtat tgtttttgagc taataataat cttggcaaga aaatcaggca      180
aaagagtaca gatactataa taaaagtatg tttcttcaag cggcatcctg ttaggtgaaa       240
atacgatttg aaataaagat tcacacagat aaatttccca atgcaaatat tatattataa      300
tgtttaagat tacacaatca tattgtctgc tattgtgatc cggtttaaag cctaatacag       360
ttttggagag ggagaccaat tatttataat aaacggtgtg agcatcctct ccagtaatga       420
aaaaatgaat tttttaaaaa aaaatgtcac aaacaacaat gtcatgcgta taagtattag      480
gtaaactgag gaggaaggaa taatgcataa cccgtttagt gaacaatcag tatcgaaaga       540
ttccgataga gaattggtgg ctgctgcaat tcagggagac ggtcaagctc tggagaagat       600
tatattaagg catcaggcat ggatttacaa catcgcattt aaaatgatta tggaccatga       660
tgatgcttgt gacattacgc aggaaatttt gattaaaacc ataaccaatc tatcgtcata       720
cgattcaaaa aaagcagctt ttcgaacctg gttgtatcgt gttgtggtca atcatgtgct       780
gagtatgaaa cggaaaaaat ttgaaagaag aatcaatgat tttgatcaat atattaattt       840
aatcgaaaaa ttgccggatc accaacagac aaatcatccg gaagctcatt ttttagcatc      900
cgaatttaaa attggttgta tgatgggaat gctcatgtgt ctcaaccgaa gtgatcgttt      960
gacattttta ctgggtgcag tttttagtat aaaagatact gttggggctg aacttatgga     1020
aatttctcga gaaaattttc gaaaaaagct gtctcgggca aaacaaaaat tatttacccca     1080 catgaatagt gtgtgcggtc atgtgaatcc cgaaagaaag tgtttatgca aaaataaata     1140
taaaaatttt gtagaaatgg gcatgttgga tggtgataat acccgatatc taaagcctga     1200
cacaatggtg gtgaaagagg ttgtggaaga aagagttaag cagttttcga ctcagtatta     1260
```

```
tgacccattt ctcactcatt ttcaggaaca accgttttat gaaccgcctg atatggtgaa      1320
atggctgcgt gatatgatcg ggcatgatga tttcaagcgt atgtttaata tacagtaagg      1380
taatatcata ttttttatat ataaaaaagg agattaacat gagaaataaa tttaaaaaag      1440
aactcaaaga atcctatcgt atggaaatgc ttggtgcggg gatttataag gggttgtcaa      1500
atcaatacag caaacgagat gctgagctaa gtcgtaaatt tttaaaattt tcaagacagg      1560
aagcgatgca tggcaggcta tttaaagagt attttttcaga acaatctttt gggcagctta      1620
gatctggttt tttctggcga ttcataggac gcatggcagc aacgctgatg aggcccttac      1680
cgttaagtaa aaaactcaaa aaatacaag tggccgaaca gcacgccgta tatagcattg       1740
aaaaaaaatt aattgaaaat cttgatcagg ggtatcgcaa atcattgag ctgattttac        1800 cgcatgaaga agcccatgcc gctctgtatg gtgacctgtt ctccgactaa atgccaagtt      1860
tgtactgggt gtacaggaca ggaaatgata ataacggggg tatgaggtcc aatgggagga     1920
ttatgtaaag ctttacataa tcgttcggtt ggacctcata ccccaatacc ataataaaaa      1980 aggagggggca gaaatgtcac aattaattga agagctcaaa tcctttcacg ttgaaatatc    2040
agatattttc cgccaggtag tggagttcgg aattacctcc gaagaaggtc agaaaaaact     2100
tcttctcgta aaatcaaaac tacttgaaca tttgaagaaa gagaatgagg aactatatcc      2160
gattctctgg aaagaagctg gaaataacat agacttaaaa cttaaattag agttgtttgc      2220
aagagatatg gatgctattg ctatgcaaac aattacattc ttcgaaaaat atactggagt     2280
aacgtctgaa aatgatttta agtctgattt taaaaagatg tatgtagcta tgacaaaaag   2340
acttaacaat gaagaaagta agctgttttc tgaatatgaa aaattgaata tccaataaat   2400
tcaatatgta aaacataacc tcaacattca gagggacagc aaaagcaggc ggtttttatt    2460
tcaagctaaa gtatgtgttc aattgccatc gacaacggtc tgtttgcttt tgctgccccct   2520 gatgccagtg ttataagaaa aaaattaatg aaaaccggaa tgcacattaa acaaaaaca    2580 ataataatta taggcgtgtt attaactata ggcggcttta tgtttgattt gtttttttgct      2640 ggtattccca atcaagatcc tacatcagaa atgacccaaa gatttaattt caataaatct    2700
gtagccaata cgatagagct aattggatta gtaagtataa taatcggaat aatagcaact    2760
attcttaaaa aaatattaaa aatgacaatc aaaatataat attccatcaa acgacaaaac    2820
ctcgaagaaa agtctccgag gttttagtcg tttatactgt tttcttgtta tatcatgttc     2880
ttagagaaat ttatcgttct caagcatata gacatataca tgccatgcat ggtttagaat    2940
agattttgcg aaatccaccg ccatattatt atcaggtacc aaccatccgc caaaatcagc    3000
gatatcgtta atcccttcca gccaatacgt gttgccatat tgcttggttt caggaactat    3060
accggccaat tcggatccga gagtggtgtc atccatctgc ttattgtggt ctgacaacca    3120
atcgccttta acgttaaaat tggttatctt gcttgcatga cgtatatcta atccgaggtt    3180
attaatggtt ccctgagata aaccggcagc atcaaacgcc attgcttcac gaccggttgc    3240
cagtgccgaa gcagttgcaa gcccgccgcc cagactgtgt ccggtaaacg acaattgcat    3300
tgccgcatca cccgtcaatc cattttgtac attgtactgt tcaacctggg cgctcaagtc    3360
ccttgcaaaa tcaactgcct tttgatattg ctctgagttc ccgaatatct gttccgcatc     3420
tgctacccag tcaacaggag acaggggttc tgttccttta taggcaacaa caaggtcatc    3480
tgtttcagtg ttttgaaaaa ctttgaaatc taaaccatca gtgccccacc agtcaatata     3540
accgccaacg gattgtactt ctacatagtt tggtgttgca aagtctgttg ctttgatatc      3600
atcgatattg gcaaagaatc ccattccaac atgcgctgct gcataatcat cccagtcgta    3660
```

```
ggcttgagcg acagcttac cgtaatcaat cgcttttca taatcagact gatttaaccc   3720
ccatgaatag tttatggtgg catatccgga tgcatacca aaggctttca ttatcagtgg   3780
tcgatccaat ttccccatga ttctgatgta ctcatgacct gaaccggtac catcgccatt   3840
atatccggag tactctatgg tcacacttcc ataagtcgtc gtcactttac ctgcaccatt   3900
taaaatacca ttcggccact gcacaatctt cgtaccattg ttttatcaa aaagctgaat   3960
atcaacatcc ctgtcagaaa tgagatcaat attgacattg gtcagccccg ccggaagttc   4020
acccacctca acaaccgcat tttgggtgat gtcttgctgg aatgttccgg agccggatct   4080
ggccggtcct tctgtgcagt tctctgtccc ttcccaggag tactcgacgg tagctgtccc   4140
tgcggcatat ccaaacgctt tcattgtcag aggttcgtct acggtaccgt aaattttgat   4200
atattcatga cctgaaccag taccatcacc gttataacct gaatactcaa tgacaaaccc   4260
accgtgaagc gtcgtgcctt tgcttggacc gtttaaaatt ccatccggcc attggacaat   4320
ttttaaaccg tgttttat caaaaagctg aatatcaaca tcctgatcac tcctcagttc   4380
aatcagaacc tcctgttttc caaccggaat gtcgccaaca ccacaacat catttcgggc   4440
gatcgcctgc tgaaacgttc cacttccgga gcaactggcc ccccccagt cgaatccggc   4500
aaatgctgaa cttgcgatga agagacttat taaacaatc aaattaattt tcatcggttt   4560
ttctagtgtt gtgttcattt ccccccctt aattaattt tttagttaat caaatgcctt   4620
agtagtacca tcacgaatat cttttatcgt ttacatgtga tccatttcga cttcggtcca   4680
ctgattgcat cagtgtcttt agtttagtct tgtaaacatc gtttagtatc tgcgcatatt   4740
atcggaaagt tcgaaaaagc acaatcaggg aaaccctaat tttgggcttc gatttccta    4800
attttccg taaatgctgt attcggttac gttaaggtct gttttttc accataagac      4860
gcaacgaaga aggtcgcttt ggtaataat tcatagttat agaatgtaat gcagaaagag   4920
gataatttga caatctctta acattaattg cccaaagatt taatatatc tatattgaca   4980
ataaacctaa atttatgaag attgtcaaaa gtgtagaaat acgctaaact aaatacaaat   5040
attgggatta taatttttcc tccaaacgct gcaattagca taataatagt tatgctaatt   5100
gtaatcaaat cttttcgaaa agaagcagta atatcttaga ttaaaataca ggaataatcg   5160
ctttactaaa aaagaacaca agtaaaatat caataacagg agaaatgctc atgacaacaa   5220
atacagcgat caatcttatt aaacgcccga gcggcggccc aatcactgcg gatctctttg   5280
ccgttgttga aaagagatg ccagctgtgg gggcgggtga gttttagtt aagcagaatc     5340
atatgtcact tgaccctgcc atgttcggtt ggatgagtcc ggacaccaat agctacattc   5400
ctcctgttgc actcggtgat gtgatgcgca gctcaggtat tggtgaagtg gtcgaaagta   5460
accacccgga ctttaaagta ggcgaccggg taatgggcat gatgggttgg cagcactatt   5520
ttctaagtaa cggccaaggg gtcaacaagg tggatgcgcc actgccggat gaagccatat   5580
tatcgatttt tgcactacct ggtttaacag ccacacaagg tttgtttaat gtcggtaaac   5640
ctaaaaaagg cgaaacgctc attgtcacag gggccgcggg ctcagtaggc tctattgttg   5700
gtcagttagc aaaagccgat ggcctgcacg tgattggtgt tgtcggcaaa gatgaaaaag   5760
ccgattggat tgtgaatgaa ttgggtttg atgctgctat taactacaag agtgacgatt    5820
tagacggtca acttgccaga cacgccgcaa acggcatcga tttgtatttt gaaaacaccg   5880
gcggcccgat tcaaaattta atcgtcgagc gtatgaatgc ccatggtcgt gtagttgttt   5940
gtggtctgat cgcagactac gacaaggaat tagcgtcacc gggcccaagc tggatcaatg   6000
```

```
tcattaaacg ccgcctgacc attcaaggat tcaccatgcc ggatcacttt catgaagtgc    6060
ctgctctgct ggcaaaacta acaccgtatg tgatggcagg taagattaaa catcgctcac    6120
atgtattaga gggattggaa tctgctatcg agggcttgaa tttattcttt accggagaga    6180
ataaaggtaa gttgatcgtc aagctttaat agaccggatc aggctgtggt ggggcaagtt    6240
aatccgatat ctgatcgtct cttttaatta ggccattgag ggattttact aacttttaat    6300
ttggtctgta gaaatatttt attacagtgg tggcaattct gctttggttt ccacctgagt    6360
tgatgtagtt gtaactggat gaagacccgg taccgattac attattatcg cattgtgctg    6420
tggtgagttt aataaaaata tctctggtta tgcgggttat ggatgcgctg tcgctgatca    6480
atttgattat ttcgatggtg cttaatgttg aaagttttga gtgggaggga gtgatgcctg    6540
atacgggaat agctgaagtg ttgattgatg aagaaaagat caaaacaatt gttgcacgtt    6600
tgggaaaaga gattaccgaa tattataaag gctctgaaaa ggagttgata gtggttgggc    6660
tgctgcgcgg ctcgtttgtg tttatggctg atctggtgcg cgagatcaaa caccctatga    6720
ttactgactt tatgacggtg tccagttatg gtgacgaaac ggtgagctcc ggtgaattca    6780
aagtggtgat ggatcttgat gaatcaattg agggacgtga catacttctg gttgaggata    6840
ttgtcgatac cggaaacact ttcagcaagg tgatccaaat gctcgaaagc agaaacccgg    6900
cttcgcttaa agtctgcact tttttgaata aaccggctcg cagagtcatc gaagtaccga    6960
tagatttctg cggtattgat attcccgatg agtttgtggt cggctacggt cttgatttgg    7020
ctcagaaata ccgcaacatt ccctatgtag gaatctataa tccggagcat aagtaggtgt    7080 catacccccgg taaggctgtc tctctgaaaa attagatctc gcgaaattcc taacaaattt    7140
cgagcagagc cagcaataaa aaaggaaata ttgataatag atgaaaaggt gcatattatc    7200
atgtagttat aaaagcgtca aaaacacatt gcgcttttca gtgtagaggt tggggttacc    7260
cttacttgga agaccgatac ctgctgcttt atagaggttc ttgattggag cgattaaacc    7320
atgccgattt ttgaatatga gtgtaaagag tgtcttaata gatttgaaaa gttagtaagg    7380
ggccaagaaa aaatctgctg ccctcagtgc aattcttaca atttaaaaaa actgatttca    7440
acctgtggta ggatctccga tgataccaaa tatgactggg gtaatcccag cctgcctaat    7500
aagcaagagt ttcaacggga aaaatttaac cacagaaatt tgggtaaaat taaacaaata    7560
gggggactcc ccaaaagcaa acgcacgaaa taaagatgca gttgtcagtg aaacgaacgg    7620
agtcatcctc cagagaccaa aaatatacct tgctacttag ggttccgtta acatttagg    7680 cctaaaagta gcgtagctgc cgtttgccgc aatctgtgtt tttgataaaa acggataaat    7740 gacttttct aaataaatca gtggattaaa aaatataatg ctttaaaaat agttggttaa    7800
gtgtgccttg tggcaaacgg caactacgct atttatgggc atagtagcat aagtctgaaa    7860
tttagttgtt tttctaaaaa tttcttcaat ataaaatcaa caattaagaa aaaataacgt    7920
ttacaggtaa gcggtgagct tcacaggaat tctatttcaa gttttaaata tgaggaagct    7980
ttgaataagc aattcagagt gaagcgtccc ttataattat agcgatttta ttaaacactt    8040
acaaaataag ttaatgccag atcgagtaaa accgcaaccg cagacatggc aaatataaac    8100
agatagttat agttttctct ggaatttctg attgaggata aacagtagat tacaacagct    8160
cgatcctcat cactaagttc atcacctttc ctgatctttg gaataagact ataatcttca    8220
atcgctcttt tacgtttctc tgaaataata tacctgtaga ggaaaaaaaa agtataccca    8280
attattccga agtaccatac gggtctgaaa tattcctgtt tcacatgctg aaatacaatc    8340
aaaattctga aagcgacggc tgataaaaca ccaagaataa aaaaaatatt aattacgtaa    8400
```

```
ccaggtaaag ttttttggaac ctctttcatt tgacgatatc cttgcttgtc atgttgaatt    8460 ttattttttgg tgacaacaac ttcaacccta taaaaactaa gagtttgtcc cattcagtca    8520
cattatgtat atatctatat accacataat tacccgtccc tcaaaaccct attcatggta    8580
agccacaatt ttaaaagtga accatttttc aatcgttttt taatttattc tacaaaaagt    8640
taaattaaag ataagaactc ctgtaaaata aagttcttta aatgtgatat ttctatttcg    8700
taaaaacgaa cgttttattg aactgtcctg gcacaatgca tcaaaaatta tagtttcatt    8760
tattgtgagt cagtggcaga taatgtgggt ccgggcttca ggatagaatc aaataatgtg    8820
gtctcagatt tgcgatgatt ccgggtccgg gtgcattata attccggtcc gctacaccta    8880
aatggaccta attaccccat tttctaaaaa ccatgctttg ctatgatttt tttcatcgtt    8940
ccatcttttg agatttgttt caaaccttcg ttgaaatcct tgatcttttct ctgataattc    9000 ttcgcttttt ttgagatggc aagatagaga ggatcctcct ttaatgaagg ttccatcggc    9060
tctaaaatct cattatattt tgggaatttc gtattaataa tatgctgagc aaccaattta    9120
tctacaatca ttaaatcaat tctacctaat actaacattt gtagagtctg tgcttctaca    9180
gtaaccggat acttttttaa ataatctgcc gcatcaaacg ctggtggatt gacataccct    9240
ttgataatcc caatcgtgta aggttttagt gcttcataac tcccattaaa tggtatattt    9300
ctatccttgc gtttataaaa gacaatgaga ctgaatggca aaggatcaga gaataatagc    9360
cactgtgccc tttcctctcg ataccaaagc gcataggttc catcggcatc tctgtctttg    9420
accatcaata gacttcttgc gaatggcacg aaatcgacct tcaccgtgta tcccattcgt    9480
tgataggcga tcttcacaat ctcagaaatg aatccataat ttggaagggt tttactctca    9540 tacgaggaa attcagtgga cgtaagtgat atttcttctt ttgcgacgac tcctccaacg    9600
gcataaatca taaatcccag tatgattaga aaatatttca gcttcatttt agctaccttt    9660
tgaattcctt tgaatgattc ctgagatgaa ctgcgaatgc caacgacata taaccagtt    9720 ataaaagccg acgagactgg ggtaacccca acctttacac taaaaagcgc aatgtgtttt    9780
tgacccattt tataactaca tgataatatg tacttttttca tattccatat gcatgcaata    9840
aaccacatta taggcaaaat gtcatctggt tttatttgaa aagatgacat tgtaattatc    9900
taaatatatc ttatggttac cataatacca cagtggtagg ggaccagtgg aagccccccc    9960
caaaagtgat cagttagaat taattttttcc ccaaaagctc tgttttaagg gctgtttaag   10020
aatctgtttg gtgaggccaa ggcaaacctg atcaggcgtg agtggctttg ccttggctcc   10080
atgtttttta aagttgtatc actatacacg tagcggattt taacccggtg gaagatgatg   10140
aatccacccc atattttaag taaaacccag tatgtaattg tcttttttcgt cacatttggg   10200 ggttcttcca ctggccccca tatacacctt cattgtgtga ttccggctgg ggtactctct   10260
tttgacaatc aatccttcaa gaagggggcgt aaggattttc tttttccagt tatggctctt   10320
tcaaaagttt ttcggggggaa atttatggag atgctacaaa cagcctatga tgaaaaaaaa   10380
cttatatttc ctgggagaac aaaatcttat ggaaccgttt ccggcttcag agctctaacc   10440
aaaattctct ggtcaaaagg ttgggtggtt tattctaaaa agccctttttc cggacctgag   10500 acagttcttg agtatctctc ccggtatact catcgggtgg cgatttcaaa taaccgtatc   10560
aaaacatgta aagatggaaa agtgactgtt acataccgaa accggaaaaa agaaaccacc   10620
gaaacactgt cgattgatgc tgttgagttt atacgtcgat ttcttttttgca tgtggtgcca   10680 cccaacttta tgagaattcg tcattttgga atatttgcca atcgctgcaa gaagaaaaat   10740
```

```
atcagtcaat gtcgcagatt tctgggcttt tctgaagtaa gacaaaaacc ggcggtaaaa   10800
tccgtagaaa ccctgatgct tgaactgaca ggaattgata taaatcgttg ccctttttgc   10860
aaaaagggtg tgatgaaaca agtttgcaat attccaaaat taaccggtaa ggggctcat    10920 gattttattc aacgccctga caggaggaat tcatcatgaa tgaagcgtag cattaattaa   10980
ctgttgttta gcctaaaatg ttcgttgaag aacaacagga taggtgcgct cattttttga   11040
taaagaggtt attcaaagga attaatttaa aaaataagc cgcgtattta aaaagggta     11100 tagtttgcgt aaggtgaaaa taaaaaaacg gggcaaaaag ttcaaaaacc atccatttaa   11160
ctcttgccag agaaatcatt cgactattta caatccccat atatattgtt aagcatttaa   11220
tacgtctaag ttcaacaaag ttttatccat catcccttgt tgtgggaaca cgggtttcac   11280
tcaatttggc attaatatt tccaggccgt tttctatgta aggaccacgg gacaatggat    11340 aaaaccctt acgttcggca actaaactaa atgaaaaaat atcatctttt catgaatggg    11400
caaaatttct taatcgactt aaatggtaaa acatctaagt atggatttta ccagaatgtt   11460
ttcgtcatat cggaagatat agaaaatgca gaacttcttg gcatagaaaa gatcagaagt   11520 gataagaag atcctccaat gattttctt gattcatacg atgaaattga tgaaatatct     11580
aatgataata tggcgttaga aaaggaagc acatattacc ttgaaaaaaa atggtggcaa    11640
ttttggaaat aattgccgaa ccaagcattc aacatagacg ggcgttacgt tgccgctaaa   11700
ttttcagctg caattttatt aatcaatcac attaactggc tttttttcgct ttgaacgccc   11760 gccagttaat ttgtcgttgg gtttcaaaat ataggaag taaatgata tcttttacag     11820 gtggagcaag aattggttgg gttaatgcaa cttggccttt tgctaaattg aatgttcaaa   11880
aaaatacaat cgaaatcaat gccacagtta ttggaaaata ttcatttaat caagatcaag   11940
taatatctat aaaaaaacat acaataattc ccgtaatagg ttggggaatt cagattgttc   12000
ataacattcc agagtatcct aagaaaataa tattttggac actgaaaaat ccgaattcag   12060
caatcacgaa gattcaaaaa actggttttt taccaaaagc agatccatcg acaataccgc   12120
ctaacattgg aatcccagtt aaatggcagg caatagtatt cattatagca ttatggaatg   12180
ctctactttt tattgatatg ggtggttttc caccagaaaa ttttaaacca ggtttatata   12240
cattattggc tattttctg cttttttactg gttcaatttc aatatggaaa ttatcgtggt    12300
tgaaacgttt aattattaaa caaggccgta gccctaatga aataaggca tttttgaatt    12360 tgatttcctt agttagtgga cttcttttag taatgatgtc catgcaaata ttattcatgg   12420
gttaaaaccc aacaatttaa taaagcggac tcaaaaaacc cgcccgcttg ttaaatcgtt   12480
gaactaagcc gctgcgcgtc agtattctcg taattccaac cacttacacc gcaccagcct   12540
tgctaataac attgcaaaaa aaatcatttt ctgattattc actctatatt aagaactcct   12600
tatattgttt tttatttatt tactaacaaa atgaggaggt aactatgggt cccattaaac   12660
atttggtaca aatccgtcat ggcctgtgcc atcattcata ttttacagga cttcacctca   12720
tacctgtaac cggcgatttt tcaagaaagt attaataatc aattgaaaaa tagttcaatt   12780 atttttagaac ggtgggttaa actataatac agttttgat ggtaggagca gtgccttaa    12840 atcgggccag gttattatg cttcctggcc gttacaatta ctctttctag cccaaagaat    12900
aattcttaga aaaatataca acacaaatag acacacaagc agagttacaa atagtcccca   12960
taactctggc aaagctatcc agccgtcgtc tgcttcaatt ttaacaacaa acttttgccc   13020
tatattttta ctgcttttg gaacaacctt gattgtatag aggattcctt tcctgcagtc   13080
atagttaaac cagtttgcat gatcaggcat ttcagtgccc tgttgcgaaa aggcaccagc   13140
```

```
ctgtcgtccc cgagcataag gaacattaag gttggaagaa actgagttct ttagatcatc   13200
accctcatag agataaagtt caatgagtga gcccgaatga ttgtcataat atgtcgaaat   13260
attaaatttt atatctgcag caggaataaa tttcagcctc atattttcgc tcattacgcc   13320
tcttaaccca tggaattttt cagtgaaata gaggtcagat tttacgtccg gtttctcgaa   13380
aagcgggccg gtataacacc ctctaaattg atttaccttt tctgcaacag caggtaattt   13440
tacctcaact aaaggaaaaa cagcgacaaa aaggcccgcc aaagctgcta aaatgataaa   13500
taaaataaga acacctccaa cacctttctc tttttttttcc atctgaaatc ctttttttgt   13560
tttatatggc ttaatctcca cgaatggaat tatgttttttt gaagcctacc aagtcttggc   13620 tacttttttca acatcctctc ttcctacttg gcaactaatg gatgtaagtc gttatgagat   13680
taactctcag atctgtactc gtacaaattc aataaattat atttccctat aattgtggat   13740
tggttcaggc tttttttaat agtcagctcc tggaaggtaa ataaatcaaa attcgcaatg   13800
catcgaaaca ataatcaatt ttccagcggt tatgtagctc acctcttatc tgtaaatggc   13860 gattttcat aagataattc aaaaacagtt gaaaactggt taattttta aatgaatct   13920 caaatatgaa ctattacaat tcatcatatg ttgtatcctt ggttttatta tattcttata   13980
gaatgttttt ccttattttt cctgtatttc ttaatccaga gtttgtctgg aattactatt   14040
agtcaggtga attatttata tcaaaaactt aaaaattttt tttctgttta cgaaagatgt   14100
ttaacatgtc tacttttact tgcccccta ccttacgtcg gattacttt tagaaaaatt   14160 atccttaatt ttttataggg atactattat ctattgactt tggaggcctt ataagtgttc   14220 ggttttttt ggtgggatag actcttttac tttccagacg tcacccttca cttcaaacca   14280
aagacgataa tagaggccta taaccgtaaa cgcattatat gtgatttcaa cgtcagtcat   14340 ataatccct cctgattttt gaattgcatc ttcgactgct ccgtctatct gaggcaagga   14400
tcgtgataga tctatcaaaa caaaccaatg aacattttct ccaactacat ctgtggctac   14460
tttctctctt tttacagaaa gatcaatgct cgtaggtgcc atgacggaaa aagtaccaac   14520
ggatcttgac atacatcctg taattcctac aacgcataac aatgtgaaaa ccatgcggaa   14580
caaatttttt ttcattcttg accttttctcc aactataatg ttctatgaaa ccgaacgctt   14640
aaaaaacccg acaaaaaaag ccgacgggat tggtttatat ttttgacaac ttagcaaaaa   14700
ccaaacctca gggcaacgaa gaacataagc gaacataaag gacatgcaaa caatacactt   14760
ttttaatttg agaaatgtgg atttagtata atttgcctgt ctctgattgt gtcttattct   14820
cggagtggtt gatttttacgt tgaggcagtt tacagataat tataaatcaa gcatttttaaa   14880 ggacatcacc tcttatctgt aaacgttatt ttttgttgat ctgttgattt aatcttaaaa   14940
aatggtgagt aaactctacc tgataattat ttaccggaat tatcaggcct gcatgataag   15000
tatgataatt gtcacgaaaa gcggcatagt aaaattaaag aggcctgtat ttacaggata   15060
tttaaatctt gaaaaagta acatttaggc atatatatta cgaaaatgg taattcggtt   15120 gcaaatgcgg ccgacgtgtt aataactaat gttgtgtgaa aaagtcattg aaaaatcaaa   15180
ccaggaggaa tgatgagaga aaagctattg tcactgcata ttaaaggaca aattaaaaaa   15240
caagaaattg ttgggtttgt ggttgaaaat gcaaagacta ttgaatcata tctggaattg   15300
ttactgacag aatatataaa accccaagga gataggtacc aattagttcg agaggtgctt   15360
ttatctaatg ttttttttaga atttggaaag aaagtcaatt tatttggcta tatcaataca   15420
agtgagcagt ggcttaaagg aaaggataaa gacgattttt ttaaaaaaat acgttcaatt   15480
```

```
ttgagaacca gaaacacatt tgcgcatgac ttaggttctt ctgctatagg agagactata   15540
gatggtgaaa tcacttttga ttacaaggtt aaaagctttc aatccgaaaa atttaaaatg   15600
cttgaatacc aagagactat aaatgatttt gaaaataact gtaatagcgt tttagaaaca   15660
attcagaaaa ttattgatag ctttgaatag gaataataaa aatcacacaa caaacaggtg   15720
caagggacaa ttaccgcggg ctttgttatt ttaaacactg tggtaatttt aacaatgatt   15780
ttttaataat caacaaggtt aatcggcggc aattgcccct gaccttcagc gttggccaaa   15840
taatgaagga ggataatcga tgactgcgag caataccgat gaatgctgtc caagattcga   15900
tcccgctccc tgggacgaga aggaactaac atgggagcac aggcgtttcg taaaagaccg   15960
ggtgatcagc tttttcata ttccgttgaa tttcggctcg gttatgaaac gtaacgtagg   16020
cgcaatcgaa gcggcggatg caaagcctga acaatggta gttctttctg acgagaactc   16080
gttctggggc gccgacgtgt atatagaggt tacaaaggac ataccgggag ccaatatggc   16140
aaccatttca ggaacgtttc tttccaaagt gttcgaggga ccatatcgga acatgcgaaa   16200
atggatcgaa gagatgaaga cgtttgtgca gagcaaagat aagcacsctg agaagttata   16260
tttttctat accacatgtc caaggtgcgc aaagaagttc ggcaagaatt acgttgctat   16320
tttggcaaag ctatagaagt ggccaacaac tggctgtaat ggattcgggc caaaaagcgg   16380
ccctcacctg tgagccagag cgttacattt cattcacaat aaacaggaga taccatgatt   16440
gcatattgcg gtttagattg ttccaaatgc gatgcacata tcgctacaat tgaaaatagt   16500
ccagcaaaaa ggattgagac tgctaaacag tggtctaaga tgtatcagca tgaaatgagt   16560
cctgaccaaa tcaattgtga tggctgcaaa tcaagtggta caaattttt tcactgtaac   16620
aactgtgaaa ttcgccagtg ctgtgtttct aaaaatgtcg aaaattgtgc agcctgcgaa   16680
gattacatct gtgacacttt agcagggttt attaagttag ctcctcaagc aggtttagcc   16740
cttgaatctc ttcgataaaa gctcgaggtt ttatagtaac ccgtcgttgc agcggaccga   16800
aagggcaagc cacttgtccc ttcggcttcg ctcggcggcc ccctaaactc catcgttaaa   16860
ggatatcacc tcttatctgt atgcgaaatt ttttaagaaa atatttaaaa acaattgaaa   16920
actgatttaa cattaaaaat gtaacttaac ctcggataca atttgagggg aggatcatat   16980
tttttctaac ggcttcgctc ggcggccccc taaactccat cgttaaagga tatcacctct   17040
tatctgtatg cgaaattttt taagaaaata tttaaaaaca attgaaaact gatttaacat   17100
taaaaatgta acttaacctc ggatacaatt tgaggggagg atcatatttt ttctaatagt   17160
aattcctcat ataagagttc tgttttttga ctcaatgggc tgcataaatc atctacaata   17220
ttttgtttac atttctcata cagaaccttt aacattgctg tatttccagt atataaataa   17280
tacttcatta gcttttgata gatattctct gcgtaaacat caactgtgag atatttttt   17340
gaatagtcta tgcattttaa aaaatctttt cgattttcat aatgttcaat tatacggcta   17400
attgcatgga ggtaagaatc ccggtaatac tctttttttt cagcaatcca atcaacataa   17460
aggtcttctg ccaaaaatgc cccttttgtat gtcgattcta ctttgagata atgatggatt   17520
gatttattca aatcagtttc gttatcctcg gcgagtatta tctcttctcg gaactcatta   17580
atatcgctcc atccatcttt ccccagatgc agtttataac cgttagcatc gtttagaata   17640
tacgatgaca tcatcccttt gatcagttcc ggttcgagta ttttttcttaa tgcagataga   17700
gttacccgta acctgtttga tgttttatta ctgtcctgtt caggccacaa catctctatc   17760
aggacttctt tggggatgaa tcctcgactg cgttctgtta atagaaattt aaacaatagt   17820
ttggcattct ggctggtcca ttttttcagca ggtatttctg tattcccacg atagagttta   17880
```

```
aactctccca ggcaggaaac ccgaagtgac ggagcgggca tctgtgtaag tatttcagag   17940
gcagcctttg agatatcagt cgacttgctt ttttgcaaat ctattaaaga ggatcttgca   18000
cacatcccca tttggttaaa aatcttcttt atatacaact gctctttacc gcttgcaaaa   18060
agctcaacca gtataggcac cacaccctct tcaccaactg agagtagaaa ataatattgg   18120
ttttcctggc atatctttat accttttaga agttttttgaa atgccatttc tttatcattt   18180
tgtgcccagt aatatcgagc ccacacaaaa tttattctat tatttagata tctaaataac   18240
tttaattctt tattagaagt ttccagtatc tgacgtgctt tttggaaatc cgattttttca   18300 atgtataaac cagcttttaaa cacgtttaac tcaaactcgg cccatggtat tttatactgg   18360
cctatgactg cctcgcattg tgaaaggttt tttaaagctt tagcatcatc accggaatgt   18420
ttatgaatct gataaaatgt aagatagcac attgccctcc cccaatcact cccgatgttt   18480
tcaaaatttc gaagactctc tttaatatgc tccgttgctt ctattgtttt atttaattca   18540
aggcaattcc gagcggcaga aaaattcagc caggcagatg gaaagaaatc ctcaaatcct   18600
ttatctctca ttaaatttag tccccttttgc gcattctcaa gtccttcaga aaaatcgccc   18660
atataataat ttgtcaatgc agtgatgtaa taattctttg tgaatagtgc ataaaaatct   18720
gaattttcga aaagttgttt ggactttttt aaaaaatcat ttgatctctg gaaattgccg   18780
gataagagat gtcgattccc tatttgagta tatatgccac cttccagaag taaccgccat   18840
tgactatctt gagggtttac tgagatcgtc atcgccttat tgtaacagag atctgcttgt   18900
tcaaacttgc cttgttgagc caaggtatca ataataaaca gatataatat cgttgttaat   18960
tctatattat ccacaaagat atcgaccgct tgtttataag tccgttcagc cttaggaaaa   19020
tcaccatcca tatgattctg atatcccagg cgcattaaac acaaagcagc tccatagggc   19080
accttatcat ttaaaaaagc ttgtgcagac tgctccagac actgaacagc ctcttgcgtt   19140
ttacctgtta gatcaagcca ttgcgccttt aaaaagttaa tccatggttc cttttggaaa   19200
tatctcgacg ggatgtgttt caggtaggat ttaattctct gtcgccgtcc tttagaccat   19260
aaaaatgttg agattttttcc gatgattcga aaagaatctt ccatctgttc acttttccaga   19320 taatactcca gggcttcttc ttcgtttcca tcctgttcca ataattgtgc cgttttttttc   19380 tgtagatcct gaatctcttc tttgcaatag ttgttatcga gttttgttct taagaaatcc   19440
tgaaaaatat ggtgatatgt aaagcaatct ttttcatcat ccaattgaaa tgtaaacaga   19500 tgtcttttttt ccaaatcaga taaaatctct tttgaattgt taatcctgag aagttgattg   19560
caaaaagcta cttttacttt tgataaaaga gaagtcttga ctaagaaatc ttttgtttca   19620
ggcggaagca tctcatacgc atttttcttct aaataggttg caataatccg gttggatcct   19680 tttatttttca ataaatcatt atctgctgtt tcctgacttt ttcctttttaa cgaatgaaag   19740 aaaaggatta aggcggcaac ccagccgcct gttttttttt ggagatcggc aaaggttctg   19800
ctctgcaatg atagctgaaa cacatctgaa taaagctttt ttatttccga aatagtaaag   19860
gcaaggtcag actctgtaag atccagaaca tctctcctga ctcgtaagct tgaaatctta   19920
attggcggtt cagcacgact gataagtaca agatgaatct tatgatgcat gttttctatt   19980
aaaaatttaa cagcacgatt gacttcatca ttatcatgaa caaggtaata atcgtccagc   20040
acaataacga actcatgttg aattcgattc tcaatctcct ttaaaagaa atgtaaaatt   20100 ttttcaacct tattaacatc ctgcaaattt tcctcaatcg aaatttctat gtcacccaga   20160
tgctcttcca tacctgcttt caagtaacta aaaaacgttt caaaatcaga atcgtattta   20220
```

```
tccaatcgat accagaccgc gggtagttta aagaaagaa cagcctgttt tacaagggtg    20280 gttttttccat atccggcacc tgcaataacc atggttaatc gtttcgtctg aatatttgac   20340
agtattggca tcaaacgatc ccgaatgatt gtttccgagg ctcctgaaaa acgaagtttt   20400
gactttaaga cttttttatt ctcgtacatt aaacaccct a ttgtagttga aacaagcaaa   20460
tgtaatttcg tttttt aaca ttaagagagc aacacttatt ctaataaaac actgggttta   20520
aataaaggtt aacaaacaat taatccaaac gtaacaggtt gttttacaga aagaaagctc   20580
caaattttat caaagtaagt tggcagttga tgttattttt cgcaatctca ttttttatga   20640
attggcatac cattggaatt ctatgttgtt gctggttttg ctttgtaat agatggacac    20700 tcgtatgttt gaggaaattt tggatttggc aaagaaaggt gaagcagtgg cgcacttaag   20760
tacgtcacac aaaagaactg cataaaaaag gaattgatag aaaaatcatt tatgagttaa   20820
caacaatcta tccaacccaa tcattcatca tcattgaaat gttatttcac cgcttcgtat   20880
cgatccgcca tagccacctc ccagaaggca ccacgctcct gtaaggtata gaccgtcaat   20940
cggcgtacga ttatataatc gttgactcag cgagcttttc atagacttat caaaaccaca   21000
gattgcacct tttgcacttc ctgtaattaa tatcatatta atgcatgatt aacatatcgt   21060
ttgttaagaa gaattattta accataaaag gaggatgtta tgaaggtact cgcactaaac   21120
gccagtcccc gcaaacaggg gcaaagtaaa accgaactca tgttgaacaa tcttgtcaag   21180
ggcatgcgtg aagctggtgc tgatgtagaa gttatcaatc ttagggacaa acaaattgag   21240
aattgtaaag ggtgcttttt ttgttggacc aagaccccgg gcatatgtgt tcaaaaagat   21300
gacatgacaa acgagctcta tccaaaatta ctggcctcgg atcttgctat ttacggaaca   21360
ccactctatt taagtacagt cagtgcttct atgaaaacat tcatagacag aacattaccc   21420
gttcttgagc cattttttcga aaagataac gaaagaatat ttcatcctta tcggcatgat   21480
cggctcaaaa tagttttttct ttccgtagca gcagtccctg gtgattcagt gttcgatcgt   21540
ttgtcttctt gggcaaatta cctgtatgct catagcggca aacttgtagc cgaaatatat   21600
agatcctgtt ccccagcatt aaacttgccg ttatatcaag aaaaatcgca agatattcta   21660
gctgctgtta cacaagccgg tcacgaactc gtgaaatcgg aaacaatttt acctgataca   21720
atggctcgca ttaagcagcc tattatggat gatgattctt ttatcgaatt gtcgaatcat   21780
atatgggagg cttgtattaa aaataaaatg actataaatg aatatattga aaaaagttg    21840 atggcagatt ctggggtctg atacccaatg gaactatttc gtacaataag tcgtatgtgc   21900
ctgatatatc cgtgtttatc aggcacataa tgaggttgtt ttaaggaatt taacagataa   21960
tatctgtaaa tcaatcaatt tataggcaaa aacgtgtttt attgttcctt atcgtacgtt   22020
tggctccact gggcttcaaa ccccttaatc ctgatattgt tactttccca atgacgacct   22080
ttacagataa ttataaatca aacatttgaa aggacatcac ctcttatctg taaacggttt   22140
tttttacaaa tttgttgaaa atttattgat actgctatgg ttttgatcaa tgtaaaaaat   22200
gattgaattt aaaagaatta tacgatagtc gataaagaaa atatcgatta gtaaaaacaa   22260 tgaattttc ccatatatag agccaaccac aagttttaag ggctataagt aaaagaatga   22320
agaaaagaat aatgatcaat ggagttgtat ttgttgcgtt gacagcaatc ccattaattg   22380
gtgagttaat tacaataaca ccaaactatg tacctggtac tggttttagt atcttgctgt   22440
atgaaccttt tgattttgcc tattcgctat tggccttaac aatattcata atagtaaata   22500
taaagattgc tattgcaagc aacacctcat tgtgggtcga tgccgtaaca tcaataggtg   22560
tatttattat atggttcatt atatcgttct tatgtgtatg tcaattgcat gttagccttg   22620
```

```
gtggtcaact atgagcatac ttataacaag gcaataaaat cattgcggac tacaaaggcc   22680
gtgtttgggt ttcactcatt tgagtttgtc gtttaagaaa ctttgtaata attactatca   22740
gcccgccgct tttcgtggct gcttattttt tatggggctt tatgaaactt ctaattatag   22800
caataattat attcttttta tgtacagtcg cctcagcaga aaaaaggcca ctttatatgt   22860
ctaaggcgag atttatagt ggtgtttata atcagaaaa tataaagaa atttgggcaa   22920 aaattgtaaa gaatctttct cctgaagagt tccaaatcct taaaatgaag ccggaatatg   22980
atatttcaac tgcagaatat attgatggtg tttatatacc tgaagatcta caagaggttt   23040
ggtttgaatt agataaaaaa ttgtcaaaag aagatcgcga gaaactaaca aaaatacaag   23100
aacatgaaat gtctaatttt cacttctcaa caggtatggg tatgagaaat agttggaaac   23160
tttggagtgg gtcacgtcta tcaaagtatt tcaatgaaat aggaatacac cacccggatg   23220
atatgtctgg cattatctta aagactttt ggtgttacat aaataataaa ccactaaaat   23280
tggagcagca aattgcattt tataacaat actgggacgt tcgtttacct cctcctttgc   23340
atacacaccc ggaacaaaac ctcattgagg ttggtgcaca agactataac acaacgaaag   23400
gaagatactt aggttatata caagtttata aaaatccaga ttctggtaaa atatggcttt   23460
atgaaaatgg caagggatgg aaaatagcta aaagtctttt ttataaaaaa tttccgcatt   23520
ggaaagaata aaaaaaggcc cataatatgg ctaaataagg attttttgaa attacggcac   23580
cctgagtaag gatcattaga aattcatcag gtgttgccgc aattgcagtc tatacagcga   23640 taaggatat cacctcttat ctttaaacgt tattttttgc gtaactattg aaaagtcgtt   23700
tatatctgtg gtgggtttgt taatataaaa acaattgaa attgcagaat aaaggggtcc   23760
acttttgact cttggtttaa atataaaggt caaacgtaga cttaaccccc atttttgatt   23820
agaagtgatt gcataattaa gtatgcgaag accaaatctt ttttttgctt cagaaagcca   23880
gtacaaccat cttttcttat cttttgaaaa ttttaacaaa aaatctttt tatgacatct   23940 ttgggtaata tgccacatgt agtttggtat atagtggcta tttgctcggg ccattttct   24000 taaatagacc ttttttacct gaaaaacaag gtcctaagac caaaaaaaaa taaaaaaata   24060
gcttttttca tattaattca agatgttgac ttggtccgac aagaatattg atacttctgc   24120
acgcccctat tcgatccgtt caccatcttt gtaagttctc tcggattctt tttttccatt   24180
ttcagaccac tcaatccgtt tcccaatctc tataccattc ttgtaagttc cctctgcttt   24240
tagttgacca ttttcatgcc aactaatcca tttcccgttc cttataccat ccttgtaagt   24300
tccctcttct tttatttgtc cattttcgta ccacagaata tatttccctt ccttataccc   24360
atccttgtaa gtttcctcct cacttatttg gccatttcg taccacagaa tatatttccc   24420
gttccttata ccatccttgt aagtttcctc cctacttatt tggccatttt cataccactc   24480 agtattttc ccgttctttt tattattctt gtaagttgtc tctatgtatt tttgactatt   24540
tccatgccac cacctaatcc atttaccgtt ccgtttacca ttcttgtatg ttgtctcgat   24600
ttttttctga ccatttcat accatgaaat atatttcccg ttcagtttac cattattgta   24660
agttgtctca ctttttttct gaccatctat aaagaacctg ataactaccc aagtgtttgg   24720
tttttcatgg ttttgtttcat aagaaatccc ttttagattt tgtaattgtg atgcatcaat   24780
gtaagtttcc tcttttttctt tttgaccatt ttcataccac gaaaaatatt tcccgtttat   24840
ttcaccattc ttaaaagtta tctcctata ttttggcca ttttcatgcc acccaatcat   24900
tgtcccgttc tctttaccat tcttggaagt tccttcctct tttttttgac cattttcata   24960
```

```
ccactgaatc catttcccgt ttattttacc aaacttgtat gttgtctctc tatattttg     25020 gccatttta taccagtaaa tagcgttccc attcagttgc ccctcttcat accaggtttc     25080
tccatcctca tatgtttcct cgcttttttt ttgaccattt tcataccaac aaatagcctt   25140
cccggtcact acaccatccc tgaaagtaaa ctcgctttt ttttgaccat tttcatacca    25200
acaaatacct ttcccgtttt ttttaccatc cttgaaaata aactcgcttt tttttggcc    25260 attttcatgc aacctaatta ctttcccggt atacggtttt ccctggttta tttcataaaa   25320
aagttcatct atcattttta attttgatgc ttcaattgtt ttactatctc catgatcaga   25380
gttacacgac acaattaaaa acaataaccc aagaactaca ataaatttt tcatctctcc    25440 acctatctta aggtcaagct cgattcgcta aatattatat gctttcactt ttatcgtttt   25500
acatttatcc aatcttttt tgtaccacta tcataataaa ttgctaattt attttttatc    25560
aagatatcgg ctaaatttct atgattataa cggacaagtt tcaaaagata tgaatcatcc   25620
tagaaaatcg gggagaaaat cggggagaaa atcggggaca gaaaatcggg aaaatcgggg   25680
acatgtataa aatcgggtat aaaatcgggg acatgtaaat aatacataat ccttgacagg   25740
gaacattgag atggggtaga ttgactaaaa cttttcatgtt ttaaggaaca taaagcatag  25800
gagacttata atgcccagaa catcacgaat gttaatccct gacgagaaaa cagcttacca   25860
tgtaatgtcg agaactgccc tggatggttt tccctttgga gatgttgaga aggataaatt   25920
tgttaatatc attaaaaggt atagtaaact ttattttgca gaaataattg gttttacaat   25980
tatggataat cactggcatt tgttagcaat aatgcacccg gagcgaaatt attccgatga   26040
agatataaaa aacagattca ttgaatttca tggtaaagat gcattctttc cacctgaacg   26100
aattccgtac tttcgagaga agtggtcgag cctttcagag tttatcagag atatcaagca   26160
gtccttttca cgcttttaca ataagcttca taacagacgt ggaactttgt ggggtgaaag   26220
atttaaaagt gtgattgttc aaaaaggtga accccttata aattgtatag cgtatattga   26280
tcttaattca atgagagccg gaatcgttaa aaaaccggat aattacagat ggagttccat   26340
cggataccat gctcagacag agaataaaga tgattttctt tctcttaatt tcggcggtgt   26400
tgaatttggt agaatggatg aaaaagaaag actcagaaga tatagaaaat atctttatga   26460
agccggggca attaataaat atgatggtaa aagcaaaaaa gttattgatc agaagatcgt   26520 tgaaaagaa agagctaata actttgaaat tacaggctcc ggaagattta tcaataaaac   26580
ccgttacttt acagactcgg gcataatagg cagtaaagag tttgttgctg aaaattatca   26640
gcggtttaaa cacatgtttc aatcgaagca tgagaagaaa cccaactcgg taaagggat    26700 tgcaggaatg tattctctta aacggctttc aatttaaaaa aatcagaaaa tcaagataat   26760
aagttctcaa taattgagga cgttgtataa atgtttaatt tttaatagtt ttctccatta   26820
tttccgtttt aacaatctta attactaata aaaaatcaca taaaataatt aatcatttt    26880 gttatgcgtt cttataattg aattgtgttg gcgctactgt ggaatttatg catagtttac   26940
atgtccctat ttccctacc tatatgttcc ctgtcaagat ttatgtatta tttgcctgtc    27000
cccagttttt ccagttttt gttatttgcc tgtccccagt tttcccagtt tttcttagta    27060
ataggactaa acacattaac ccaaaataaa ttttccaata aaataataag ctactttttt   27120
tccacattat cctcaacct tttctatttt tcaagtggtt caaacattcc gccacaatat    27180
cattgactaa tactgctatg attttttaca ctatggtaca gccagaattc aagaacgcaa   27240
ccactaaaat ttgactatta ttatctttat tctattctat tttcgttttt cgtcccacat   27300
atatttattt tgtgcatatc agtactatgg gttctattaa acatttggta caaattcgtc   27360
```

```
acagccagaa acatctttta tatcgtacag gagctcacct cttatctgta aaggttattt    27420
tttgttgaac ggttgattta ctattgatca agtggactta ttattcccaa aacatgaaat    27480
tattatatat gaagagagat acataataga tcaaacgaaa ggttagacaa cctgaaaata    27540
actaaaattt cagaattatg ctgctagcag caaaacagtt ataattcgac aaaatcttaa    27600
catggacttt tcacatattt taatatatct tattgataat aaaacaaaat caatgattat    27660
tgccaaaatt agcaaaatgc gctaaaacaa ctataaatgt gaggatttat aattttttcct   27720 caaaaagctg ctagcagcat aataaaattg ttgtgtttca aatactatga atgaaaataa    27780
agaaataatt aaaaaaggaa cattcctcta cgatggttct gtaatcacgg atattaaaat    27840
tgttaaaact aatattcggt atggatcttg tgattacgag gatgaacctg aatatagaga    27900
tgatttcgaa ggggaattct ataatatcga atttggctct actactgaac gaggtaaatt    27960
tgtatctggt tctctctccc acacatcatt acaagaggca atatcggaag ccgaaaaggc    28020
aactaatttc acggtaactt gggataaata aaagtcccaa aacacaacaa taaggtgcaa    28080
gggacaatta ccgcggcttt gttctattga atgctgccgt gactttaaac tgtaattttt    28140
tattaatctt caaggtcaat cggcggtaat tgcccctgac cttaagcgtt caatccccta    28200
aagagacaaa tattgaggaa tatgtgaata gatcaaattt tgattttgaa agatttcaat    28260
ctgcaaaaag attaaaaata actaagagtt caaaccatg ccctactgaa attggcgatg     28320
agatttacca gaacggaatt tttgaattca atatttcaaa acttatcgaa tatattaaga    28380
ataatactga taaatttgaa cttatagaag ttgagattga cgattttcct aaagaatttt    28440
catcattaaa tgagatgcat gtggaatcaa cagaccattc tcaacctgta ataatcgctg    28500
agatttctcc aggactttat aatttgattg atggcaatca taggatggaa aaagcacgta    28560
taaagggatt gacttgtatt aatgcattca agttaatgt ggaccagcac ataaaattct      28620
taactgataa agatgcgtat ttaaagtaca tcgagtactg gaatggtaaa ataaggcatt    28680
gatattatag acaagaccga aattcactca gactggtgtt acgctgccgc tacacaccgg    28740
ctggtgatgc tgacgttccg ggcctgggtt aaggatcatt cgaaattcat caggtggtgc    28800
cgcaattgca gtcgatacga cgataaagga tttcacctct tatct                    28845
```

<210> SEQ ID NO 2
<211> LENGTH: 1698
<212> TYPE: DNA
<213> ORGANISM: Unknown
<220> FEATURE:
<223> OTHER INFORMATION: PlaG sequence

<400> SEQUENCE: 2

```
atgaacacaa cactagaaaa accgatgaaa attaatttga ttgttttaat aagtctcttc      60
atcgcaagtt cagcatttgc cggattcgac tggggggggg ccagttgctc cggaagtgga     120
acgtttcagc aggcgatcgc ccgaaatgat gttgtggttg ttggcgacat tccggttgga     180
aaacaggagg ttctgattga actgaggagt gatcaggatg ttgatattca gcttttttgat    240 aaaaacaccg gtttaaaaat tgtccaatgg ccggatggaa tttttaaacgg tccaagcaaa    300 ggcacgacgc ttcacggtgg gtttgtcatt gagtattcag gttataacgg tgatggtact    360
ggttcaggtc atgaatatat caaaatttac ggtaccgtag acgaacctct gacaatgaaa     420
gcgtttggat atgccgcagg gacagctacc gtcgagtact cctgggaagg gacagagaac    480
tgcacagaag gaccggccag atccggctcc ggaacattcc agcaagacat cacccaaaat    540
```

```
gcggttgttg aggtgggtga acttccggcg gggctgacca atgtcaatat tgatctcatt      600
tctgacaggg atgttgatat tcagcttttt gataaaaaca atggtacgaa gattgtgcag      660
tggccgaatg gtatttaaaa tggtgcaggt aaagtgacga cgacttatgg aagtgtgacc      720
atagagtact ccggatataa tggcgatggt accggttcag gtcatgagta catcagaatc      780
atggggaaat tggatcgacc actgataatg aaagcctttg gtatgcatc cggatatgcc      840 accataaact attcatgggg gttaaatcag tctgattatg aaaaagcgat tgattacggt      900
aagctgtccg ctcaagccta cgactgggat gattatgcag cagcgcatgt tggaatggga      960
ttctttgcca atatcgatga tatcaaagca acagactttg caacaccaaa ctatgtagaa     1020
gtacaatccg ttggcggtta tattgactgg tggggcactg atggtttaga tttcaaagtt     1080
tttcaaaaca ctgaaacaga tgaccttgtt gttgcctata aggaacagaa accctgtct     1140 cctgttgact gggtagcaga tgcggaacag atattcggga actcagagca atatcaaaag     1200
gcagttgatt ttgcaaggga cttgagcgcc caggttgaac agtacaatgt acaaaatgga     1260
ttgacgggtg atgcggcaat gcaattgtcg tttaccggac acagtctggg cggcgggctt     1320
gcaactgctt cggcactggc aaccggtcgt gaagcaatgg cgtttgatgc tgccggttta     1380
tctcagggaa ccattaataa cctcggatta gatatacgtc atgcaagcaa gataaccaat     1440
tttaacgtta aaggcgattg gttgtcagac acaataagc agatggatga caccactctc     1500
ggatccgaat tggccggtat agttcctgaa accaagcaat atggcaacac gtattggctg     1560
gaagggatta acgatatcgc tgattttggc ggatggttgg tacctgataa taatatggcg     1620
gtggatttcg caaaatctat tctaaaccat gcatggcatg tatatgtcta tgcttgag     1680 aacgataaat ttctctaa                                                    1698
```

<210> SEQ ID NO 3
<211> LENGTH: 837
<212> TYPE: DNA
<213> ORGANISM: Unknown
<220> FEATURE:
<223> OTHER INFORMATION: MP1aG sequence

<400> SEQUENCE: 3

```
ttaaatcagt ctgattatga aaaagcgatt gattacggta agctgtccgc tcaagcctac       60
gactgggatg attatgcagc agcgcatgtt ggaatgggat tctttgccaa tatcgatgat      120
atcaaagcaa cagactttgc aacaccaaac tatgtagaag tacaatccgt tggcggttat      180
attgactggt ggggcactga tggtttagat ttcaaagttt ttcaaaacac tgaaacagat      240
gaccttgttg ttgcctataa aggaacagaa accctgtctc ctgttgactg ggtagcagat      300
gcggaacaga tattcgggaa ctcagagcaa tatcaaaagg cagttgattt tgcaagggac      360
ttgagcgccc aggttgaaca gtacaatgta caaaatggat tgacgggtga tgcggcaatg      420
caattgtcgt ttaccggaca cagtctgggc ggcgggcttg caactgcttc ggcactggca      480
accggtcgtg aagcaatggc gtttgatgct gccggtttat ctcagggaac cattaataac      540
ctcggattag atatacgtca tgcaagcaag ataaccaatt ttaacgttaa aggcgattgg      600
ttgtcagacc acaataagca gatggatgac accactctcg gatccgaatt ggccggtata      660
gttcctgaaa ccaagcaata tggcaacacg tattggctgg aagggattaa cgatatcgct      720
gattttggcg gatggttggt acctgataat aatatggcgg tggatttcgc aaaatctatt      780
ctaaaccatg catggcatgt atatgtctat gcttgaga cgataaatt tctctaa            837
```

```
<210> SEQ ID NO 4
<211> LENGTH: 565
<212> TYPE: PRT
<213> ORGANISM: Unknown
<220> FEATURE:
<223> OTHER INFORMATION: phospholipase/lipase PlaG AA

<400> SEQUENCE: 4

Met Asn Thr Thr Leu Glu Lys Pro Met Lys Ile Asn Leu Ile Val Leu
1               5                   10                  15

Ile Ser Leu Phe Ile Ala Ser Ser Ala Phe Ala Gly Phe Asp Trp Gly
            20                  25                  30

Gly Ala Ser Cys Ser Gly Ser Gly Thr Phe Gln Gln Ala Ile Ala Arg
        35                  40                  45

Asn Asp Val Val Val Gly Asp Ile Pro Val Gly Lys Gln Glu Val
    50                  55                  60

Leu Ile Glu Leu Arg Ser Asp Gln Asp Val Asp Ile Gln Leu Phe Asp
65                  70                  75                  80

Lys Asn Thr Gly Leu Lys Ile Val Gln Trp Pro Asp Gly Ile Leu Asn
                85                  90                  95

Gly Pro Ser Lys Gly Thr Thr Leu His Gly Phe Val Ile Glu Tyr
            100                 105                 110

Ser Gly Tyr Asn Gly Asp Gly Thr Gly Ser Gly His Glu Tyr Ile Lys
        115                 120                 125

Ile Tyr Gly Thr Val Asp Glu Pro Leu Thr Met Lys Ala Phe Gly Tyr
    130                 135                 140

Ala Ala Gly Thr Ala Thr Val Glu Tyr Ser Trp Glu Gly Thr Glu Asn
145                 150                 155                 160

Cys Thr Glu Gly Pro Ala Arg Ser Gly Ser Gly Thr Phe Gln Gln Asp
                165                 170                 175

Ile Thr Gln Asn Ala Val Val Glu Val Gly Glu Leu Pro Ala Gly Leu
            180                 185                 190

Thr Asn Val Asn Ile Asp Leu Ile Ser Asp Arg Asp Val Asp Ile Gln
        195                 200                 205

Leu Phe Asp Lys Asn Asn Gly Thr Lys Ile Val Gln Trp Pro Asn Gly
    210                 215                 220

Ile Leu Asn Gly Ala Gly Lys Val Thr Thr Thr Tyr Gly Ser Val Thr
225                 230                 235                 240

Ile Glu Tyr Ser Gly Tyr Asn Gly Asp Gly Thr Gly Ser Gly His Glu
                245                 250                 255

Tyr Ile Arg Ile Met Gly Lys Leu Asp Arg Pro Leu Ile Met Lys Ala
            260                 265                 270

Phe Gly Tyr Ala Ser Gly Tyr Ala Thr Ile Asn Tyr Ser Trp Gly Leu
        275                 280                 285

Asn Gln Ser Asp Tyr Glu Lys Ala Ile Asp Tyr Gly Lys Leu Ser Ala
    290                 295                 300

Gln Ala Tyr Asp Trp Asp Asp Tyr Ala Ala Ala His Val Gly Met Gly
305                 310                 315                 320

Phe Phe Ala Asn Ile Asp Asp Ile Lys Ala Thr Asp Phe Ala Thr Pro
                325                 330                 335

Asn Tyr Val Glu Val Gln Ser Val Gly Gly Tyr Ile Asp Trp Trp Gly
            340                 345                 350

Thr Asp Gly Leu Asp Phe Lys Val Phe Gln Asn Thr Glu Thr Asp Asp
        355                 360                 365

Leu Val Val Ala Tyr Lys Gly Thr Glu Pro Leu Ser Pro Val Asp Trp
```

```
                  370                 375                 380
Val Ala Asp Ala Glu Gln Ile Phe Gly Asn Ser Glu Gln Tyr Gln Lys
385                 390                 395                 400

Ala Val Asp Phe Ala Arg Asp Leu Ser Ala Gln Val Glu Gln Tyr Asn
                405                 410                 415

Val Gln Asn Gly Leu Thr Gly Asp Ala Ala Met Gln Leu Ser Phe Thr
            420                 425                 430

Gly His Ser Leu Gly Gly Leu Ala Thr Ala Ser Ala Leu Ala Thr
            435                 440                 445

Gly Arg Glu Ala Met Ala Phe Asp Ala Ala Gly Leu Ser Gln Gly Thr
450                 455                 460

Ile Asn Asn Leu Gly Leu Asp Ile Arg His Ala Ser Lys Ile Thr Asn
465                 470                 475                 480

Phe Asn Val Lys Gly Asp Trp Leu Ser Asp His Asn Lys Gln Met Asp
                485                 490                 495

Asp Thr Thr Leu Gly Ser Glu Leu Ala Gly Ile Val Pro Glu Thr Lys
            500                 505                 510

Gln Tyr Gly Asn Thr Tyr Trp Leu Glu Gly Ile Asn Asp Ile Ala Asp
            515                 520                 525

Phe Gly Gly Trp Leu Val Pro Asp Asn Asn Met Ala Val Asp Phe Ala
        530                 535                 540

Lys Ser Ile Leu Asn His Ala Trp His Val Tyr Val Tyr Met Leu Glu
545                 550                 555                 560

Asn Asp Lys Phe Leu
                565

<210> SEQ ID NO 5
<211> LENGTH: 278
<212> TYPE: PRT
<213> ORGANISM: Unknown
<220> FEATURE:
<223> OTHER INFORMATION: phospholipase/lipase MPlaG AA

<400> SEQUENCE: 5

Leu Asn Gln Ser Asp Tyr Glu Lys Ala Ile Asp Tyr Gly Lys Leu Ser
1               5                   10                  15

Ala Gln Ala Tyr Asp Trp Asp Tyr Ala Ala Ala His Val Gly Met
            20                  25                  30

Gly Phe Phe Ala Asn Ile Asp Asp Ile Lys Ala Thr Asp Phe Ala Thr
                35                  40                  45

Pro Asn Tyr Val Glu Val Gln Ser Val Gly Gly Tyr Ile Asp Trp Trp
50                  55                  60

Gly Thr Asp Gly Leu Asp Phe Lys Val Phe Gln Asn Thr Glu Thr Asp
65                  70                  75                  80

Asp Leu Val Val Ala Tyr Lys Gly Thr Glu Pro Leu Ser Pro Val Asp
                85                  90                  95

Trp Val Ala Asp Ala Glu Gln Ile Phe Gly Asn Ser Glu Gln Tyr Gln
                100                 105                 110

Lys Ala Val Asp Phe Ala Arg Asp Leu Ser Ala Gln Val Glu Gln Tyr
            115                 120                 125

Asn Val Gln Asn Gly Leu Thr Gly Asp Ala Ala Met Gln Leu Ser Phe
            130                 135                 140

Thr Gly His Ser Leu Gly Gly Leu Ala Thr Ala Ser Ala Leu Ala
145                 150                 155                 160

Thr Gly Arg Glu Ala Met Ala Phe Asp Ala Ala Gly Leu Ser Gln Gly
```

-continued

```
                        165                 170                 175
Thr Ile Asn Asn Leu Gly Leu Asp Ile Arg His Ala Ser Lys Ile Thr
            180                 185                 190

Asn Phe Asn Val Lys Gly Asp Trp Leu Ser Asp His Asn Lys Gln Met
        195                 200                 205

Asp Asp Thr Thr Leu Gly Ser Glu Leu Ala Gly Ile Val Pro Glu Thr
    210                 215                 220

Lys Gln Tyr Gly Asn Thr Tyr Trp Leu Glu Gly Ile Asn Asp Ile Ala
225                 230                 235                 240

Asp Phe Gly Gly Trp Leu Val Pro Asp Asn Asn Met Ala Val Asp Phe
                245                 250                 255

Ala Lys Ser Ile Leu Asn His Ala Trp His Val Tyr Val Tyr Met Leu
            260                 265                 270

Glu Asn Asp Lys Phe Leu
        275

<210> SEQ ID NO 6
<211> LENGTH: 29
<212> TYPE: DNA
<213> ORGANISM: Artificial Sequence
<220> FEATURE:
<223> OTHER INFORMATION: forward primer

<400> SEQUENCE: 6
ccccatatgt taaatcagtc tgattatga                                    29

<210> SEQ ID NO 7
<211> LENGTH: 30
<212> TYPE: DNA
<213> ORGANISM: Artificial Sequence
<220> FEATURE:
<223> OTHER INFORMATION: reverse primer

<400> SEQUENCE: 7
cccctcgaga aatttatcgt tctcaagcat                                   30
```